United States Patent
Fidock et al.

(10) Patent No.: US 7,063,971 B2
(45) Date of Patent: Jun. 20, 2006

(54) PHOSPHODIESTERASE ENZYMES

(75) Inventors: Mark D. Fidock, Sandwich (GB); Nicola M. Robas, Sandwich (GB)

(73) Assignee: Pfizer Inc., New York, NY (US)

( * ) Notice: Subject to any disclaimer, the term of this patent is extended or adjusted under 35 U.S.C. 154(b) by 164 days.

(21) Appl. No.: 10/746,197

(22) Filed: Dec. 24, 2003

(65) Prior Publication Data

US 2004/0126863 A1    Jul. 1, 2004

Related U.S. Application Data

(63) Continuation of application No. 09/663,542, filed on Sep. 15, 2000, now abandoned.

(60) Provisional application No. 60/177,517, filed on Jan. 21, 2000.

(30) Foreign Application Priority Data

Sep. 17, 1999   (GB) .................................. 9922124.4

(51) Int. Cl.
  *C12N 9/00*    (2006.01)
  *C12N 5/00*    (2006.01)
  *C12N 15/63*   (2006.01)
  *C07K 1/00*    (2006.01)
  *C12P 21/06*   (2006.01)

(52) U.S. Cl. .................. 435/183; 435/69.1; 435/320.1; 435/325; 435/455; 536/23.1; 536/23.5; 530/350

(58) Field of Classification Search ................ 530/350; 435/69.1, 183, 320.1, 325, 455; 536/23.1, 536/23.5
See application file for complete search history.

(56) References Cited

OTHER PUBLICATIONS

Hetman et al, Cloning and characterization of two splice variants of human phosphodiesterase 11A. Proc Natl Acad Sci U S A. 97(23):12891-5. Nov. 7, 2000.*

Yuasa et al. Isolation and Characterization of Two Novel Phosphodiesterase PDE11A Variants Showing Unique Structure and Tissue-specific Expression J. Biol. Chem., vol. 275, Issue 40, 31469-31479, Oct. 6, 2000.*

Ngo, Computational complexity Protein structure prediction and the Levinthal paradox in The Protein Folding Problem and Tertiary Structure Prediction, Merz et al. (eds.), Birkhauser Boston: Boston, MA, pp. 433 and 492-495, 1994.*

Rudinger Characteristics of amino acids as components of a peptide hormone sequence (in Peptide Hormones, Parsons (ed.), University Park Press: Baltimore, MD, pp. 1-7, 1976).*

* cited by examiner

*Primary Examiner*—Sumesh Kaushal

(74) *Attorney, Agent, or Firm*—Gregg C. Benson; Nicholas I. Slepchuk, Jr.

(57) ABSTRACT

Amino acid sequences and nucleotide sequences relating to PDEXV are described. In a preferred aspect, the amino acid sequence comprises the sequence presented as SEQ ID NO:1.

13 Claims, 4 Drawing Sheets

FIG. 1A

Alignment of nucleotide sequence of PDE11A3 (PDEXV) with variant PDE11A2 and also PDE11A1

Here, the amino acid sequence of PDE11A2 is SEQ ID NO:3 and the nucleotide sequence is SEQ ID NO:4, and the amino acid sequence of PDE11A1 is SEQ ID NO:5 and the nucleotide sequence is SEQ ID NO:6.

```
PDE11A2    ----------------------------------------------------------
PDE11A1    ----------------------------------------------------------
PDE11A3    GGTCCGAGATGCTGAAGCAGGCAAGAAGACCTTTATTCAGAAATGTGCTCAGTGCCACAC

PDE11A2    ----------------------------------------------------------
PDE11A1    ----------------------------------------------------------
PDE11A3    AGTGGAAAAAGGTGAAAATCACAAGACTGGTCCAAATCTCTGGGGCCTCTTTGGCTGAAA

PDE11A2    ----------------------------------------------------------
PDE11A1    ----------------------------------------------------------
PDE11A3    AACAGGAAAAGCACCAGGATTTTCTTATACAGAGGCAAACAAAAACAAAGGATCGACGAT

PDE11A2    ----------------------------------------------------------
PDE11A1    ----------------------------------------------------------
PDE11A3    TCAATGATGAAATCGACAAGCTGACTGGATACAAGACAAAATCATTATTGTGCATGCCTA

PDE11A2    ---------------------------------------------------------G
PDE11A1    ----------------------------------------------------------
PDE11A3    TCCGAAGCAGTGATGGTGAGATTATTGGTGTGCCCAAGCGATAAATAAGATTCCTGAAG

PDE11A2    CAATAGGAAGCCATGGAACAGCCAGAAAGGTTATGCAGATGTATCTTCCATTTTGTGGAA
PDE11A1    ----------------------------------------------------------
PDE11A3    GAGCTCCATTTACTGAAGATGATGAAAAAGTTATGCAGATGTATCTTCCATTTTGTGGAA

PDE11A2    TCGCCATATCTAACGCTCAGCTCTTTGCTGCCTCAAGGAAAGAATATGAAAGAAGCAGAG
PDE11A1    ----------------------------------------------------------
PDE11A3    TCGCCATATCTAACGCTCAGCTCTTTGCTGCCTCAAGGAAAGAATATGAAAGAAGCAGAG

PDE11A2    CTTTGCTAGAGGTGGTTAATGACCTCTTTGAAGAACAGACTGACCTGGAGAAAATTGTCA
PDE11A1    ---TGGAA-AGATGTTACTTCATCTCCCAGGTTTGCTCACTGCA------AATACAATCC
PDE11A3    CTTTGCTAGAGGTGGTTAATGACCTCTTTGAAGAACAGACTGACCTGGAGAAAATTGTCA
            **  *  **  ** *     * *   * ***    *        ****      **  **

PDE11A2    AGAAAATAATGCATCGGGCCCAAACTCTGCTGAAATGTGAACGCTGTTCTGTTTTACTCC
PDE11A1    TGAGAACTGAACTAGGGCCTTAAAGTC--CTGACATG----CATGGCTTGGTTTTG----
PDE11A3    AGAAAATAATGCATCGGGCCCAAACTCTGCTGAAATGTGAGCGCTGTTTCTGTTTTACTCC
            ** **      *   ** *  ***  **  ****  ***      *  *    *****

PDE11A2    TAGAGGACATCGAATCACCAGTGGTGAAATTTACCAAATCCTTTGAATTGATGTCCCCAA
PDE11A1    TGGATTGCCTCTCTCAACAGGTGGTGAAATTTACCAAATCCTTTGAATTGATGTCCCCAA
PDE11A3    TAGAGGACATCGAATCACCAGTGGTGAAATTTACCAAATCCTTTGAATTGATGTCCCCAA
            *  **   *  **       **  ************************************

PDE11A2    AGTGCAGTGCTGATGCTGAGAACAGTTTCAAAGAAAGCATGGAGAAATCATCATACTCCG
PDE11A1    AGTGCAGTGCTGATGCTGAGAACAGTTTCAAAGAAAGCATGGAGAAATCATCATACTCCG
PDE11A3    AGTGCAGTGCTGATGCTGAGAACAGTTTCAAAGAAAGCATGGAGAAATCATCATACTCCG
            ************************************************************

PDE11A2    ACTGGCTAATAAATAACAGCATTGCTGAGCTGGTTGCTTCAACAGGCCTTCCAGTGAACA
PDE11A1    ACTGGCTAATAAATAACAGCATTGCTGAGCTGGTTGCTTCAACAGGCCTTCCAGTGAACA
PDE11A3    ACTGGCTAATAAATAACAGCATTGCTGAGCTGGTTGCTTCAACAGGCCTTCCAGTGAACA
```

FIG. 1B

```
PDE11A2    TCAGTGATGCCTACCAGGATCCGCGCTTTGATGCAGAGGCAGACCAGATATCTGGTTTTC
PDE11A1    TCAGTGATGCCTACCAGGATCCGCGCTTTGATGCAGAGGCAGACCAGATATCTGGTTTTC
PDE11A3    TCAGTGATGCCTACCAGGATCCGCGCTTTGATGCAGAGGCAGACCAGATATCTGGTTTTC
           ************************************************************

PDE11A2    ACATAAGATCTGTTCTTTGTGTCCCTATTTGGAATAGCAACCACCAAATAATTGGAGTGG
PDE11A1    ACATAAGATCTGTTCTTTGTGTCCCTATTTGGAATAGCAACCACCAAATAATTGGAGTGG
PDE11A3    ACATAAGATCTGTTCTTTGTGTCCCTATTTGGAATAGCAACCACCAAATAATTGGAGTGG
           ************************************************************

PDE11A2    CTCAAGTGTTAAACAGACTTGATGGGAAACCTTTTGATGATGCGGATCAACGACTTTTTG
PDE11A1    CTCAAGTGTTAAACAGACTTGATGGGAAACCTTTTGATGATGCAGATCAACGACTTTTTG
PDE11A3    CTCAAGTGTTAAACAGACTTGATGGGAAACCTTTTGATGATGCAGATCAACGACTTTTTG
           ****************************************** ****************

PDE11A2    AGGCTTTTGTCATCTTTTGTGGACTTGGCATCAACAACACAATTATGTATGATCAAGTGA
PDE11A1    AGGCTTTTGTCATCTTTTGTGGACTTGGCATCAACAACACAATTATGTATGATCAAGTGA
PDE11A3    AGGCTTTTGTCATCTTTTGTGGACTTGGCATCAACAACACAATTATGTATGATCAAGTGA
           ************************************************************

PDE11A2    AGAAGTCCTGGGCCAAGCAGTCTGTGGCTCTTGATGTGCTATCATACCATGCAACATGTT
PDE11A1    AGAAGTCCTGGGCCAAGCAGTCTGTGGCTCTTGATGTGCTATCATACCATGCAACATGTT
PDE11A3    AGAAGTCCTGGGCCAAGCAGTCTGTGGCTCTTGATGTGCTATCATACCATGCAACATGTT
           ************************************************************

PDE11A2    CAAAAGCTGAAGTTGACAAGTTTAAGGCAGCCAACATCCCTCTGGTGTCAGAACTTGCCA
PDE11A1    CAAAAGCTGAAGTTGACAAGTTTAAGGCAGCCAACATCCCTCTGGTGTCAGAACTTGCCA
PDE11A3    CAAAAGCTGAAGTTGACAAGTTTAAGGCAGCCAACATCCCTCTGGTGTCAGAACTTGCCA
           ************************************************************

PDE11A2    TCGATGACATTCATTTTGATGACTTTTCTCTCGACGTTGATGCCATGATCACAGCTGCTC
PDE11A1    TCGATGACATTCATTTTGATGACTTTTCTCTCGACGTTGATGCCATGATCACAGCTGCTC
PDE11A3    TCGATGACATTCATTTTGATGACTTTTCTCTCGACGTTGATGCCATGATCACAGCTGCTC
           ************************************************************

PDE11A2    TCCGGATGTTCATGGAGCTGGGGATGGTACAGAAATTTAAAATTGACTATGAGACACTGT
PDE11A1    TCCGGATGTTCATGGAGCTGGGGATGGTACAGAAATTTAAAATTGACTATGAGACACTGT
PDE11A3    TCCGGATGTTCATGGAGCTGGGGATGGTACAGAAATTTAAAATTGACTATGAGACACTGT
           ************************************************************

PDE11A2    GTAGGTGGCTTTTGACAGTGAGGAAAAACTATCGGATGGTTCTATACCACAACTGGAGAC
PDE11A1    GTAGGTGGCTTTTGACAGTGAGGAAAAACTATCGGATGGTTCTATACCACAACTGGAGAC
PDE11A3    GTAGGTGGCTTTTGACAGTGAGGAAAAACTATCGGATGGTTCTATACCACAACTGGAGAC
           ************************************************************

PDE11A2    ATGCCTTCAACGTGTGTCAGCTGATGTTCGCGATGTTAACCACTGCTGGGTTTCAAGACA
PDE11A1    ATGCCTTCAACGTGTGTCAGCTGATGTTCGCGATGTTAACCACTGCTGGGTTTCAAGACA
PDE11A3    ATGCCTTCAACGTGTGTCAGCTGATGTTCGCGATGTTAACCACTGCTGGGTTTCAAGACA
           ************************************************************

PDE11A2    TTCTGACCGAGGTGGAAATTTTAGCGGTGATTGTGGGATGCCTGTGTCATGACCTCGACC
PDE11A1    TTCTGACCGAGGTGGAAATTTTAGCGGTGATTGTGGGATGCCTGTGTCATGACCTCGACC
PDE11A3    TTCTGACCGAGGTGGAAATTTTAGCGGTGATTGTGGGATGCCTGTGTCATGACCTCGACC
           ************************************************************

PDE11A2    ACAGGGGAACCAACAATGCCTTCCAAGCTAAGAGTGGCTCTGCCCTGGCCCAACTCTATG
PDE11A1    ACAGGGGAACCAACAATGCCTTCCAAGCTAAGAGTGGCTCTGCCCTGGCCCAACTCTATG
PDE11A3    ACAGGGGAACCAACAATGCCTTCCAAGCTAAGAGTGGCTCTGCCCTGGCCCAACTCTATG
           ************************************************************

PDE11A2    GAACCTCTGCTACCTTGGAGCATCACCATTTCAACCACGCCGTGATGATCCTTCAAAGTG
PDE11A1    GAACCTCTGCTACCTTGGAGCATCACCATTTCAACCACGCCGTGATGATCCTTCAAAGTG
PDE11A3    GAACCTCTGCTACCTTGGAGCATCACCATTTCAACCACGCCGTGATGATCCTTCAAAGTG
           ************************************************************

PDE11A2    AGGGTCACAATATCTTTGCTAACCTGTCCTCCAAGGAATATAGTGACCTTATGCAGCTTT
PDE11A1    AGGGTCACAATATCTTTGCTAACCTGTCCTCCAAGGAATATAGTGACCTTATGCAGCTTT
PDE11A3    AGGGTCACAATATCTTTGCTAACCTGTCCTCCAAGGAATATAGTGACCTTATGCAGCTTT
           ************************************************************
```

FIG. 1C

```
PDE11A2    TGAAGCAGTCAATATTGGCAACAGACCTCACGCTGTACTTTGAGAGGAGAACTGAATTCT
PDE11A1    TGAAGCAGTCAATATTGGCAACAGACCTCACGCTGTACTTTGAGAGGAGAACTGAATTCT
PDE11A3    TGAAGCAGTCAATATTGGCAACAGACCTCACGCTGTACTTTGAGAGGAGAACTGAATTCT
           ************************************************************

PDE11A2    TTGAACTTGTCAGTAAAGGAGAATACGATTGGAACATCAAAAACCATCGTGATATATTTC
PDE11A1    TTGAACTTGTCAGTAAAGGAGAATACGATTGGAACATCAAAAACCATCGTGATATATTTC
PDE11A3    TTGAACTTGTCAGTAAAGGAGAATACGATTGGAACATCAAAAACCATCGTGATATATTTC
           ************************************************************

PDE11A2    GATCAATGTTAATGACAGCCTGTGACCTTGGAGCCGTGACCAAACGGTGGGAGATCTCCA
PDE11A1    GATCAATGTTAATGACAGCCTGTGACCTTGGAGCCGTGACCAAACGGTGGGAGATCTCCA
PDE11A3    GATCAATGTTAATGACAGCCTGTGACCTTGGAGCCGTGACCAAACGGTGGGAGATCTCCA
           ************************************************************

PDE11A2    GACAGGTGGCAGAACTTGTAACCAGTGAGTTCTTCGAACAAGGAGATCGGGAGAGATTAG
PDE11A1    GACAGGTGGCAGAACTTGTAACCAGTGAGTTCTTCGAACAAGGAGATCGGGAGAGATTAG
PDE11A3    GACAGGTGGCAGAACTTGTAACCAGTGAGTTCTTCGAACAAGGAGATCGGGAGAGATTAG
           ************************************************************

PDE11A2    AGCTCAAACTCACTCCTTCAGCAATTTTTGATCGGAACGGAAGGATGAACTGCCTCGGT
PDE11A1    AGCTCAAACTCACTCCTTCAGCAATTTTTGATCGGAACGGAAGGATGAACTGCCTCGGT
PDE11A3    AGCTCAAACTCACTCCTTCAGCAATTTTTGATCGGAACCGGAAGGATGAACTGCCTCGGT
           ************************************************************

PDE11A2    TGCAACTGGAGTGGATTGATAGCATCTGCATGCCTTTGTATCAGGCACTGGTGAAGGTCA
PDE11A1    TGCAACTGGAGTGGATTGATAGCATCTGCATGCCTTTGTATCAGGCACTGGTGAAGGTCA
PDE11A3    TGCAACTGGAGTGGATTGATAGCATCTGCATGCCTTTGTATCAGGCACTGGTGAAGGTCA
           ************************************************************

PDE11A2    ACGTGAAACTGAAGCCGATGCTAGATTCAGTAGCTACAAACAGAAGTAAGTGGGAAGAGC
PDE11A1    ACGTGAAACTGAAGCCGATGCTAGATTCAGTAGCTACAAACAGAAGTAAGTGGGAAGAGC
PDE11A3    ACGTGAAACTGAAGCCGATGCTAGATTCAGTAGCTACAAACAGAAGTAAGTGGGAAGAGC
           ************************************************************

PDE11A2    TACACCAAAAACGACTGCTGGCCTCAACTGCCTCATCCTCCTCCCCTGCCAGTGTTATGG
PDE11A1    TACACCAAAAACGACTGCTGGCCTCAACTGCCTCATCCTCCTCCCCTGCCAGTGTTATGG
PDE11A3    TACACCAAAAACGACTGCTGGCCTCAACTGCCTCATCCTCCTCCCCTGCCAGTGTTATGG
           ************************************************************

PDE11A2    TAGCCAAGGAAGACAGGAACTAA-ACCTCCAGGTCAGCTGCAGCTGCAAAATGACTACAG
PDE11A1    TAGCCAAGGAAGACAGGAACTAA-ACCTCCAGGTCAGCTGCAGCTGCAAAATGACTACAG
PDE11A3    TAGCCAAGGAAGACAGGAACTAATAACTCGAGGCATGC----------------------
           *********************** *  ***  ***  **

PDE11A2    CCTGAAGGGCCATTTTCAGTCCAGCAATGTCATCCTTTTGTTCTTTTAGCTCAGAAAGAC
PDE11A1    CCTGAAGGGCCATTTTCAGTCCAGCAATGTCATCCTTTTGTTCTTTTAGCTCAGAAAGAC
PDE11A3    ------------------------------------------------------------

PDE11A2    CTAACATCTCAAGGATGCACTGGGAACCATGCCTGGGCTTTCACCTTGAAGCATGGTCAG
PDE11A1    CTAACATCTCAAGGATGCACTGGGAACCATGCCTGGGCTTTCACCTTGAAGCATGGTCAG
PDE11A3    ------------------------------------------------------------

PDE11A2    CAGCA
PDE11A1    CAGCA
PDE11A3    -----
```

FIG. 2
Alignment of peptide sequence of PDE11A3 (PDEXV) with splice variants PDE11A2 and PDE11A1

Here, the amino acid sequence of PDE11A2 is SEQ ID NO:3 and the nucleotide sequence is SEQ ID NO:4, and the amino acid sequence of PDE11A1 is SEQ ID NO:5 and the nucleotide sequence is SEQ ID NO:6.

```
PDE11A3    MLKQARRPLPRNVLSATQWKKVKITRLVQISGASLAKKQKKHQDFLIQKQTKTKDRRFND
PDE11A1    ------------------------------------------------------------
PDE11A2    ------------------------------------------------------------

PDE11A3    EIDKLTGYKTKSLLCMPIRSSDGEIIGVAQAIMKIPEGAPPTEDDEKVMQMYLPFCGIAI
PDE11A1    ------------------------------------------------------------
PDE11A2    ---------------------------------------------MQMYLPFCGIAI

PDE11A3    SNAQLFAASRKEYERSRALLEVVMDLFEEQTDLEKIVKKIMHRAQTLLKCERCSVLLLED
PDE11A1    ------------------------------------------------------------
PDE11A2    SNAQLFAASRKEYERSRALLEVVMDLFEEQTDLEKIVKKIMHRAQTLLKCERCSVLLLED

PDE11A3    IESPVVKFTKSFELMSPKCSADAENSFKESMEKSSYSDWLIMNSIAELVASTGLPVNISD
PDE11A1    --------------MSPKCSADAENSFKESMEKSSYSDWLIMNSIAELVASTGLPVNISD
PDE11A2    IESPVVKFTKSFELMSPKCSADAENSFKESMEKSSYSDWLIMNSIAELVASTGLPVNISD
                         ************************************************

PDE11A3    AYQDPRFDAEADQISGPHIRSVLCVPIWNSNHQIIGVAQVLNRLDGKPFDDADQRLFEAF
PDE11A1    AYQDPRFDAEADQISGPHIRSVLCVPIWNSNHQIIGVAQVLNRLDGKPFDDADQRLFEAF
PDE11A2    AYQDPRFDAEADQISGPHIRSVLCVPIWNSNHQIIGVAQVLNRLDGKPFDDADQRLFEAF
           ************************************************************

PDE11A3    VIFCGLGINNTIMYDQVKKSWAKQSVALDVLSYHATCSKAEVDKFKAANIPLVSELAIDD
PDE11A1    VIFCGLGINNTIMYDQVKKSWAKQSVALDVLSYHATCSKAEVDKFKAANIPLVSELAIDD
PDE11A2    VIFCGLGINNTIMYDQVKKSWAKQSVALDVLSYHATCSKAEVDKFKAANIPLVSELAIDD
           ************************************************************

PDE11A3    IHFDDFSLDVDAMITAALRMFMELGMVQKFKIDYSTLCRWLLTVRKNYRMVLYHNWRHAF
PDE11A1    IHFDDFSLDVDAMITAALRMFMELGMVQKFKIDYSTLCRWLLTVRKNYRMVLYHNWRHAF
PDE11A2    IHFDDFSLDVDAMITAALRMFMELGMVQKFKIDYSTLCRWLLTVRKNYRMVLYHNWRHAF
           ************************************************************

PDE11A3    NVCQLMFAMLTTAGFQDILTEVEILAVIVGCLCHDLDHRGTNNAFQAKSGSALAQLYGTS
PDE11A1    NVCQLMFAMLTTAGFQDILTEVEILAVIVGCLCHDLDHRGTNNAFQAKSGSALAQLYGTS
PDE11A2    NVCQLMFAMLTTAGFQDILTEVEILAVIVGCLCHDLDHRGTNNAFQAKSGSALAQLYGTS
           ************************************************************

PDE11A3    ATLEHHHFHHAVMILQSEGHNIFANLSSKEYSDLMQLLKQSILATDLTLYFERRTEFFEL
PDE11A1    ATLEHHHFHHAVMILQSEGHNIFANLSSKEYSDLMQLLKQSILATDLTLYFERRTEFFEL
PDE11A2    ATLEHHHFHHAVMILQSEGHNIFANLSSKEYSDLMQLLKQSILATDLTLYFERRTEFFEL
           ************************************************************

PDE11A3    VSKGEYDWNIKNHRDIFRSMLMTACDLGAVTKPWEISRQVAELVTSEFFEQGDRERLELK
PDE11A1    VSKGEYDWNIKNHRDIFRSMLMTACDLGAVTKPWEISRQVAELVTSEFFEQGDRERLELK
PDE11A2    VSKGEYDWNIKNHRDIFRSMLMTACDLGAVTKPWEISRQVAELVTSEFFEQGDRERLELK
           ************************************************************

PDE11A3    LTPSAIFDRNRKDELPRLQLEWIDSICNPLYQALVKVNVKLKPMLDSVATNRSKWEELHQ
PDE11A1    LTPSAIFDRNRKDELPRLQLEWIDSICNPLYQALVKVNVKLKPMLDSVATNRSKWEELHQ
PDE11A2    LTPSAIFDRNRKDELPRLQLEWIDSICNPLYQALVKVNVKLKPMLDSVATNRSKWEELHQ
           ************************************************************

PDE11A3    KRLLASTASSSSPASVMVAKEDRN
PDE11A1    KRLLASTASSSSPASVMVAKEDRN
PDE11A2    KRLLASTASSSSPASVMVAKEDRN
           ************************
```

PHOSPHODIESTERASE ENZYMES

CROSS REFERENCE TO RELATED APPLICATIONS

This application is continuation of U.S. patent application Ser. No. 09/663,542, filed Sep. 15, 2000, now abandoned, which claims priority to a U.S. Provisional Patent Application Ser. No. 60/177,517, filed Jan. 21, 2000, which claims benefit of a U.K. Provisional Patent Application No. 9922124, filed Sep. 17, 1999.

BACKGROUND OF THE PRESENT INVENTION

The present invention relates to an enzyme. The present invention also relates to a nucleotide sequence encoding same.

In particular, the present invention relates to a novel nucleic acid sequence encoding a novel phosphodiesterase enzyme.

The present invention also relates to the use of the novel nucleic acid and amino acid sequences in the diagnosis and treatment of disease.

The present invention also relates to the use of the novel nucleic acid and amino acid sequences to evaluate and/or to screen for agents that can modulate phosphodiesterase activity.

The present invention further relates to genetically engineered host cells that comprise or express the novel nucleic acid and amino acid sequences to evaluate and/or to screen for agents that can modulate phosphodiesterase activity.

BACKGROUND ART

Cyclic nucleotides, such as cAMP and cGMP, are important intracellular second messengers. Cyclic nucleotide phosphodiesterases—otherwise known as PDEs—are a family of enzymes that catalyse the degradation of cyclic nucleotides and, in doing so, are one of the cellular components that regulate the concentration of cyclic nucleotides.

In recent years, at least seven PDE enzymes (such as PDEI–PDEVII), as well as many subtypes of these enzymes, have been defined based on substrate affinity and cofactor requirements (Beavo J A and Reifsnyder D H, Trends Pharmacol. Sci. 11:150 [1990]; Beavo J, In: Cyclic Nucleotide Phosphodiesterases: Structure, Regulation and Drug Action., Beavo J and Housley M D (Eds.). Wiley:Chichester, pp. 3–15 [1990]).

Examples of PDEs include: PDEI which is a $Ca^{2+}$/Calmodulin-dependent PDE; PDEII which is a cGMP stimulated PDE; PDEIII which is a cGMP inhibited PDE; PDEIV which is a high affinity cAMP-specific PDE; and PDEV which is a cGMP specific PDE.

Each PDE family may contain two or more isoforms (i.e. there may be two or more PDE isoenzymes). By way of example, mammalian PDE IV, the homologue of the *Drosophila* Dunce gene (Chen C N et al., Proc. Nat. Acad. Sci. (USA) 83:9313 [1986]), is known to have four isoforms in the rat (Swinnen J V et al., Proc. Nat. Acad. Sci. (USA) 86:5325 [1989]). Human PDEs are also known to occur as isoforms and have splice variants. For example, the cloning of one human isoform of PDEIV from monocytes was reported in 1990 (Livi G P et al., Mol. Cell. Bio., 10:2678 [1990]). By way of further example, other workers have independently cloned three splice variants of PDEIV, which are now designated hPDEIV-B1, hPDEIV-B2, and hPDEIV-B3.

Teachings on cyclic nucleotide phosphodiesterases can also be found in U.S. Pat. No. 5,932,423 and U.S. Pat. No. 5,932,465.

Teachings on a further cyclic nucleotide phosphodiesterase—namely CN PCDE8—can be found in WO-A-97/35989. According to WO-A-97/35989, CN PCDE8 has two isozymes—which were designated CN PCDE8A and CN PCDE8B. The term "isozyme" is sometimes referred to in the art as "isoform".

According to WO-A-97/35989, many inhibitors of different PDEs have been identified and some have undergone clinical evaluation. For example, PDEIII inhibitors are being developed as antithrombotic agents, as antihypertensive agents and as cardiotonic agents useful in the treatment of congestive heart failure. Rolipram, a PDEIII inhibitor, has been used in the treatment of depression and other inhibitors of PDEIII are undergoing evaluation as anti-inflammatory agents. Rolipram has also been shown to inhibit lipopolysaccharide (LPS) induced TNF-alpha which has been shown to enhance HIV-1 replication in vitro. Therefore, rolipram may inhibit HIV-1 replication (Angel et al 1995 AIDS 9:1137–44). Additionally, based on its ability to suppress the production of TNF alpha and beta and interferon gamma, rolipram has been shown to be effective in the treatment of encephalomyelitis, the experimental animal model for multiple sclerosis (Sommer et al, 1995 Nat Med 1:244–248) and may be effective in the treatment of tardive dyskinesia (Sasaki et al, 1995 Eur J Phamacol 282:71–76).

According to WO-A-97/35989, there are also non-specific PDE inhibitors such as theophylline, used in the treatment of bronchial asthma and other respiratory diseases, and pentoxifylline, used in the treatment of intermittent claudication and diabetes-induced peripheral vascular disease. Theophylline is thought to act on airway smooth muscle function as well as in an anti-inflammatory or immunomodulatory capacity in the treatment of respiratory diseases (Banner et al 1995 Respir J 8:996–1000) where it is thought to act by inhibiting both CN PDE cAMP and cGMP hydrolysis (Banner et al 1995 Monaldi Arch Chest Dis 50:286–292). Pentoxifylline, also known to block TNF-alpha production, may inhibit HIV-1 replication (Angel et al supra). A list of CN PDE inhibitors is given in Beavo 1995 supra.

It has been suggested that selective inhibitors of PDEs, in addition to their isozymes and their subtypes, will lead to more effective therapy with fewer side effects. For example, see the teachings in the reviews of Wieshaar R E et al, (J. Med. Chem., 28:537 [1985]), Giembycz M A (Biochem. Pharm., 43:2041 [1992]) and Lowe J A and Cheng J B (Drugs of the Future, 17:799–807 [1992]).

Thus, for some applications it is desirable to have a selective inhibition of an individual type of PDE. Hence, the cloning and expression of a novel PDE would greatly aid the discovery of selective inhibitors.

SUMMARY ASPECTS OF THE PRESENT INVENTION

Aspects of the present invention are presented in the claims and in the following commentary.

In a broad aspect, the present invention relates to novel amino acid sequences. In this regard, we have identified a specific novel amino acid sequence and it is to be understood that the invention covers that sequence as well as novel variants, fragments, derivatives, homologues thereof.

In another broad aspect, the present invention relates to novel nucleic acid sequences. In this regard, we have identified a specific novel nucleic acid sequence and it is to be understood that the invention covers that sequence as well as novel variants, fragments, derivatives, homologues thereof.

Thus, in brief, some aspects of the present invention relate to:
1. Novel amino acids.
2. Novel nucleotide sequences.
3. Assays using said novel sequences.
4. Compounds/compositions identified by use of said assays.
5. Expression systems comprising or expressing said novel sequences.
6. Methods of treatment based on said novel sequences.
7. Pharmaceutical compositions based on said novel sequences.

Other aspects concerning the amino acid sequence of the present invention and/or the nucleotide sequence of the present invention include: a construct comprising or capable of expressing the sequences of the present invention; a vector comprising or capable of expressing the sequences of the present invention; a plasmid comprising or capable of expressing the sequences of present invention; a tissue comprising or capable of expressing the sequences of the present invention; an organ comprising or capable of expressing the sequences of the present invention; a transformed host comprising or capable of expressing the sequences of the present invention; a transformed organism comprising or capable of expressing the sequences of the present invention. The present invention also encompasses methods of expressing the same, such as expression in a micro-organism; including methods for transferring same.

For ease of reference, aspects of the present invention are now discussed under appropriate section headings. However, the teachings under each section are not necessarily limited to each particular section.

In the following commentary references to "nucleotide sequence of the present invention" and "amino acid sequence of the present invention" refer respectively to any one or more of the nucleotide sequences presented or discussed herein and to any one or more of the amino acid sequences presented or discussed herein. Also, and as used herein, "amino acid sequence" refers to peptide or protein sequences and may refer to portions thereof. In addition, the term "amino acid sequence of the present invention" is synonymous with the phrase "polypeptide sequence of the present invention". Also, the term "nucleotide sequence of the present invention" is synonymous with the phrase "polynucleotide sequence of the present invention".

BRIEF DESCRIPTION OF THE FIGURES

FIG. 1 shows the alignment of the nucleotide sequence of PDE11A3 (PDEXV, SEQ ID NO:2) with variant PDE11A2 (SEQ ID NO:4) and also PDE11A1 (SEQ ID NO:6).

FIG. 2 shows the alignment of the peptide sequence of PDE11A3 (PDEXV, SEQ ID NO:1) with variant PDE11A2 (SEQ ID NO:3) and also PDE11A1 (SEQ ID NO:5).

DETAILED ASPECTS OF THE PRESENT INVENTION

According to one aspect of the present invention there is provided an amino acid sequence comprising the sequence presented as SEQ ID No. 1, or a variant, homologue, fragment or derivative thereof, wherein the amino acid sequence is capable of displaying PDE activity.

SEQ ID No. 1 is the amino acid sequence of PDEXV (which we sometimes call PDE11A3). PDEXV has 684 amino acids. Without wishing to be bound by theory, the amino acid sequences associated with putative cGMP binding motifs (X2) have been underlined. The presence of two cGMP binding motifs provides the potential for differential regulation of splice variants.

Preferably, the amino acid sequence of the present invention has two cGMP binding motifs.

For convenience, we now present a Table indicating the codes used for the amino acids.

| AMINO ACID | THREE LETTER ABBREVIATION | ONE LETTER SYMBOL |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

For convenience, the PDE of the present invention is sometimes referred to as PDEXV.

We believe that PDE of the present invention is a truncated version of PDE11A1. The sequences for PDE11A1 are presented in the attached sequence listings, along with PDE11A2 which we believe is a variant according to the PDE of the present invention.

The PDE of the present invention is capable of catalysing the degradation of cAMP and/or cGMP.

For SEQ ID No. 1 any one or more of the amino acids may be an analogue thereof.

The term "analogue" as used herein means a sequence having a sequence similar to that of SEQ ID No. 1 l but wherein non-detrimental (i.e. not detrimental to enzymatic activity) amino acid substitutions or deletions have been made.

According to a second aspect of the present invention there is provided a nucleotide sequence encoding the amino acid sequence of the present invention.

Preferably, the nucleotide sequence comprises the sequence presented as SEQ ID No. 2, or a variant, homologue, fragment or derivative thereof, wherein the nucleotide sequence codes for an amino acid sequence that is capable of displaying PDE activity.

According to a third aspect of the present invention there is provided a nucleotide sequence that is capable of hybridising to the nucleotide sequence according to the present invention, or a sequence that is complementary thereto.

According to a fourth aspect of the present invention there is provided a nucleotide sequence that is capable of hybridising to the nucleotide sequence according to the third aspect of the present invention, or a sequence that is complementary thereto.

According to a fifth aspect of the present invention there is provided a vector comprising the nucleotide sequence according to the present invention.

According to a sixth aspect of the present invention there is provided a host cell into which has been incorporated the nucleotide sequence according to the present invention.

According to a seventh aspect of the present invention there is provided an assay method for identifying an agent that can affect PDEXV activity or expression thereof, the assay method comprising contacting an agent with an amino acid according to the present invention or a nucleotide sequence according to the present invention; and measuring the activity or expression of PDEXV; wherein a difference between a) PDE activity or expression in the absence of the agent and b) PDE activity or expression in the presence of the agent is indicative that the agent can affect PDEXV activity or expression.

Preferably the assay is to screen for agents useful in the treatment of a cardiovascular disorder and/or disorders found in any one or more of the corpus cavernosum, kidney, liver, skeletal muscle, testis, prostate.

According to an eighth aspect of the present invention there is provided a process comprising the steps of: (a) performing the assay according to the present invention; (b) identifying one or more agents that do affect PDEXV activity or expression; and (c) preparing a quantity of those one or more identified agents.

According to a ninth aspect of the present invention there is provided a method of affecting in vivo PDEXV activity or expression with an agent; wherein the agent is capable of affecting PDEXV activity or expression in an in vitro assay method; wherein the in vitro assay method is the assay method of the present invention.

According to a tenth aspect of the present invention there is provided the use of an agent in the preparation of a pharmaceutical composition for the treatment of a disease or condition associated with PDEXV, the agent is capable of having an effect on the activity or expression of PDE when assayed in vitro by the assay method of the present invention.

According to an eleventh aspect of the present invention there is provided an enzyme capable of having an immunological reaction with an antibody raised against PDEXV.

According to a twelfth aspect of the present invention there is provided a nucleotide sequence coding for a PDE, wherein the nucleotide sequence is obtainable from NCIMB 41025.

According to a thirteenth aspect of the present invention there is provided a PDE wherein the PDE is expressable from a nucleotide sequence obtainable from NCIMB 41025.

According to a fourteenth aspect of the present invention there is provided the use of an agent which has an effect on the activity of PDEXV or the expression thereof in the preparation of a pharmaceutical composition for the treatment of a disease or condition associated with PDEXV.

According to a further aspect of the present invention there is provided a nucleotide sequence selected from:
(a) the nucleotide sequence presented as SEQ ID No. 2;
(b) a nucleotide sequence that is a variant, homologue, derivative or fragment of the nucleotide sequence presented as SEQ ID No. 2;
(c) a nucleotide sequence that is the complement of the nucleotide sequence set out as SEQ ID No. 2;
(d) a nucleotide sequence that is the complement of a variant, homologue, derivative or fragment of the nucleotide sequence presented as SEQ ID No. 2;
(e) a nucleotide sequence that is capable of hybridising to the nucleotide sequence set out as SEQ ID No. 2;
(f) a nucleotide sequence that is capable of hybridising to a variant, homologue, derivative or fragment of the nucleotide sequence presented as SEQ ID No. 2;
(g) a nucleotide sequence that is the complement of a nucleotide sequence that is capable of hybridising to the nucleotide sequence set out as SEQ ID No. 2;
(h) a nucleotide sequence that is the complement of a nucleotide sequence that is capable of hybridising to a variant, homologue, derivative or fragment of the nucleotide sequence presented as SEQ ID No. 2;
(i) a nucleotide sequence that is capable of hybridising to the complement of the nucleotide sequence set out as SEQ ID No. 2;
(j) a nucleotide sequence that is capable of hybridising to the complement of a variant, homologue, derivative or fragment of the nucleotide sequence presented as SEQ ID No. 2;
(k) a nucleotide sequence which is degenerate as a result of the genetic code to the nucleotides defined in (a), (b), (c), (d), (e), (f), (g), (h), (i), or (j);
(l) a nucleotide sequence comprising any one of (a), (b), (c), (d), (e), (f), (g), (h), (i), (j) and/or (k).

Other aspects of the present invention are now presented below.

An isolated nucleotide sequence or an isolated protein sequence according to the present invention.

A substantially pure nucleotide sequence or a substantially pure protein sequence according to the present invention.

An assay method for identifying an agent that can affect the expression pattern of the nucleotide sequence of the present invention or the activity of the expression product thereof, the assay method comprising: exposing the nucleotide sequence of the present invention or the expression product ("EP") thereof with an agent; determining whether the agent modulates (such as affects the expression pattern or activity) the nucleotide sequence of the present invention or the expression product thereof.

An agent identified by the assay method of the present invention.

An agent identified by the assay method of the present invention, which agent has hitherto been unknown to have a PDE modulation effect in accordance with the present invention.

A process comprising the steps of: (a) performing the assay of the present invention; (b) identifying one or more agents that affect the expression pattern of the nucleotide sequence of the present invention or the activity of the expression product thereof; (c) preparing a quantity of those one or more identified agents.

A process comprising the steps of: (a) performing the assay according to the present invention; (b)identifying one or more agents that affect the expression pattern of the nucleotide sequence of the present invention or the activity of the expression product thereof; (c) preparing a pharmaceutical composition comprising one or more identified agents.

A process comprising the steps of: (a) performing the assay according to the present invention; (b) identifying one or more agents that affect the expression pattern of the nucleotide sequence of the present invention or the activity of the expression product thereof; (c) modifying one or more identified agents to cause a different effect on the expression pattern of the nucleotide sequence of the present invention or the activity of the expression product thereof.

Use of an agent identified by an assay according to the present invention in the manufacture of a medicament which affects the expression pattern of the nucleotide sequence of the present invention or the activity of the expression product thereof.

A method of treating a target (which target can be a mammal, preferably a human), which method comprises delivering (such as administering or exposing) to the target an effective amount of an agent capable of modulating the expression pattern of the nucleotide sequence of the present invention or the activity of the expression product thereof.

A method of treating a target (which target can be a mammal, preferably a human), which method comprises delivering (such as administering or exposing) to the target an effective amount of an agent identified by an assay according to the present invention.

A method of inducing an immunological response in a subject, the method comprising administering to the subject the nucleotide sequence of the present invention or the expression product thereof.

PDEXV (PDE11A3)

As explained above, the present invention relates to a novel PDE enzyme—which we have called PDEXV (which may otherwise be expressed as PDE11A3)—and to a nucleotide sequence encoding same. The present invention also relates to the use of the novel nucleic acid and amino acid sequences in the diagnosis and treatment of disease. The present invention also relates to the use of the novel nucleic acid and amino acid sequences to evaluate and/or to screen for agents that can modulate phosphodiesterase activity. The present invention further relates to genetically engineered host cells that comprise or express the novel nucleic acid and amino acid sequences to evaluate and/or to screen for agents that can modulate phosphodiesterase activity.

PDEXV is believed to be present in, and obtainable from, a variety of sources.

By way of example, PDEXV is found in the cardiovascular system, the corpus cavernosum, kidney, liver, skeletal muscle, testis, prostate.

We also believe that PDEXV is also present in a number of other sources—such as for example: bovine, ovine, porcine, and equine.

Preferably, the present invention covers mammalian PDEXV which includes but is not limited to any of the above sources.

More preferably, the present invention covers human PDEXV.

The PDEXV may be the same as the naturally occurring form—for this aspect, preferably the PDEXV is the non-native amino acid sequence (i.e. it is not present in its natural environment)—or is a variant, homologue, fragment or derivative thereof. In addition, or in the alternative, the PDEXV is isolated PDEXV and/or purified PDEXV. The PDEXV can be obtainable from or produced by any suitable source, whether natural or not, or it may be synthetic, semi-synthetic or recombinant.

The PDEXV coding sequence may be the same as the naturally occurring form—for this aspect, preferably the PDEXV coding sequence is the non-native nucleotide sequence (i.e. it is not present in its natural environment)—or is a variant, homologue, fragment or derivative thereof. In addition, or in the alternative, the PDEXV coding sequence is an isolated PDEXV coding sequence and/or a purified PDEXV coding sequence. The PDEXV coding sequence can be obtainable from or produced by any suitable source, whether natural or not, or it may be synthetic, semi-synthetic or recombinant.

PDEXV and/or its coding sequence and/or a sequence capable of hybridising thereto is/are useful for testing the selectivity of drug candidates between different PDEs.

PDEXV is believed to be able to catalyse the conversion of cGMP to GMP and/or cAMP to AMP.

cGMP is the messenger in the male erectile response. Accordingly, inhibiting the activity of PDEXV is likely to increase the concentration of cGMP present and so may enhance the male erectile response.

Thus, PDEXV and/or its coding sequence and/or a sequence capable of hybridising thereto may be useful for screening drug candidates for the treatment of male erectile dysfunction. In addition, it is believed that PDEXV and/or its coding sequence and/or a sequence capable of hybridising thereto may be useful for screening drug candidates for the treatment of female sexual dysfunction.

Preferred aspects of the present invention include a recombinant PDEXV enzyme and a recombinant nucleotide sequence encoding a PDEXV enzyme.

Preferably the recombinant PDEXV enzyme and/or the recombinant nucleotide sequence of the present invention are a recombinant mammalian PDEXV enzyme and/or a recombinant mammalian nucleotide sequence.

Preferably the recombinant PDEXV enzyme and/or the recombinant nucleotide sequence of the present invention are a recombinant human PDEXV enzyme and/or a recombinant human nucleotide sequence.

Either or both of the nucleotide sequence coding for PDEXV or the enzyme PDEXV itself may be used to screen for agents that can affect PDEXV activity. In particular, the nucleotide sequence coding for PDEXV or PDEXV itself may be used to screen for agents that can inhibit PDEXV activity. In addition, the nucleotide sequence coding for PDEXV or the enzyme PDEXV itself may be used to screen for agents that selectively affect PDEXV activity, such as selectively inhibit PDEXV activity.

Furthermore, the nucleotide sequence coding for PDEXV or a sequence that is complementary thereto may also be used in assays to detect the presence of PDEXV coding sequences in human cells. These assays would provide information regarding the tissue distribution of this enzyme and its biological relevance with respect to particular disease states.

The present invention also covers antibodies to PDEXV (including a derivative, fragment, homologue or variant thereof). The antibodies for PDEXV may be used in assays to detect the presence of PDEXV in human cells. These assays would provide information regarding the tissue distribution of this enzyme and its biological relevance with respect to particular disease states.

In particular, any one or more of the PDEXV isozymes, the nucleotide sequences coding for same, the nucleotide sequences that are complementary to same, and the antibodies directed to same may be used in assays to screen for agents that selectively affect one of the isozymes. These assays would provide information regarding the tissue distribution of each of the isozymes and to provide information regarding the biological relevance of each of the isozymes with respect to particular disease states. These assays would also allow workers to test for and identify agents that are useful to affect the expression of or activity of PDEXV—such as in a particular tissue or in a particular disease state.

Polypeptide of the Present Invention

The term "polypeptide"—which is interchangeable with the term "protein"—includes single-chain polypeptide molecules as well as multiple-polypeptide complexes where individual constituent polypeptides are linked by covalent or non-covalent means.

Preferably, the polypeptide of the present invention is a single-chain polypeptide.

Polypeptides of the present invention may be in a substantially isolated form. It will be understood that the polypeptide may be mixed with carriers or diluents which will not interfere with the intended purpose of the polypeptide and still be regarded as substantially isolated. A polypeptide of the present invention may also be in a substantially purified form, in which case it will generally comprise the polypeptide in a preparation in which more than 90%, e.g. 95%, 98% or 99% of the polypeptide in the preparation is a polypeptide of the present invention. Polypeptides of the present invention may be modified for example by the addition of histidine residues to assist their purification or by the addition of a signal sequence to promote their secretion from a cell as discussed below.

Polypeptides of the present invention may be produced by synthetic means (e.g. as described by Geysen et al., 1996) or recombinantly, as described below.

In a preferred embodiment, the amino acid sequence per se the present invention does not cover the native PDEXV according to the present invention when it is in its natural environment and when it has been expressed by its native nucleotide coding sequence which is also in its natural environment and when that nucleotide sequence is under the control of its native promoter which is also in its natural environment. For ease of reference, we have called this preferred embodiment the "non-native amino acid sequence".

The terms "variant", "homologue" or "fragment" in relation to the amino acid sequence for the enzyme of the present invention include any substitution of, variation of, modification of, replacement of, deletion of or addition of one (or more) amino acid from or to the sequence providing the resultant enzyme has PDEXV activity, preferably being at least as biologically active as the enzyme shown in the attached sequence listings. In particular, the term "homologue" covers homology with respect to structure and/or function. With respect to sequence homology, preferably there is at least 75%, more preferably at least 85%, more preferably at least 90% homology to the sequence shown as SEQ ID No. 1 More preferably there is at least 95%, more preferably at least 98%, homology to the sequence shown as SEQ ID No. 1.

Preferably, the variant, homologue or fragment of the present invention comprises at least 25 contiguous amino acids, preferably at least 45 contiguous amino acids, preferably at least 65 contiguous amino acids, preferably at least 85 contiguous amino acids, preferably at least 105 contiguous amino acids, preferably at least 125 contiguous amino acids, preferably at least 145 contiguous amino acids, preferably at least 165 contiguous amino acids, preferably at least 185 contiguous amino acids, of the following N terminal sequence:

```
MLKQARRPLFRNVLSATQWKKVKITRLVQISGASLAEKQEKHQDFLIQRQTKTKDRRFND  (SEQ ID NO:7)

EIDKLTGYKTKSLLCMPIRSSDGEIIGVAQAINKIPEGAPFTEDDEKVMQMYLPFCGIAI

SNAQLFAASRKEYERSRALLEVVNDLFEEQTDLEKIVKKIMHRAQTLLKCERCSVLLLED

IESPVVKFTKSFEL
```

Typically, for the variant, homologue or fragment of the present invention, the types of amino acid substitutions that could be made should maintain the hydrophobicity/hydrophilicity of the amino acid sequence. Amino acid substitutions may be made, for example from 1, 2 or 3 to 10, 20 or 30 substitutions provided that the modified sequence retains the ability to act as a PDE enzyme in accordance with present invention. Amino acid substitutions may include the use of non-naturally occurring analogues, for example to increase blood plasma half-life.

The amino acid sequence of the present invention may be produced by expression of a nucleotide sequence coding for same in a suitable expression system.

In addition, or in the alternative, the protein itself could be produced using chemical methods to synthesize a PDE amino acid sequence, in whole or in part. For example, peptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic peptides may be confirmed by amino acid analysis or sequencing (e.g., the Edman degradation procedure).

Direct peptide synthesis can be performed using various solid-phase techniques (Roberge J Y et al (1995) Science 269: 202–204) and automated synthesis may be achieved, for example, using the ABI 43 1 A Peptide Synthesizer (Perkin Elmer) in accordance with the instructions provided by the manufacturer. Additionally, the amino acid sequence of PDE, or any part thereof, may be altered during direct synthesis and/or combined using chemical methods with a sequence from other subunits, or any part thereof, to produce a variant polypeptide.

In another embodiment of the invention, a PDE natural, modified or recombinant sequence may be ligated to a heterologous sequence to encode a fusion protein. For example, for screening of peptide libraries for inhibitors of PDE activity, it may be useful to encode a chimeric PDE protein expressing a heterologous epitope that is recognised by a commercially available antibody. A fusion protein may also be engineered to contain a cleavage site located between a PDE sequence and the heterologous protein sequence, so that the PDE may be cleaved and purified away from the heterologous moiety.

PDE may also be expressed as a recombinant protein with one or more additional polypeptide domains added to facilitate protein purification. Such purification facilitating domains include, but are not limited to, metal chelating peptides such as histidine-tryptophan modules that allow purification on immobilised metals (Porath J (1992) Protein Expr Purif 3-.26328 1), protein A domains that allow purification on immobilised immunoglobulin, and the domain utilised in the FLAGS extension/affinity purification system (Immunex Corp, Seattle, Wash.). The inclusion of a cleavable linker sequence such as Factor XA or enterokinase (Invitrogen, San Diego, Calif.) between the purification domain and PDE is useful to facilitate purification.

A specific amino acid sequence of PDEXV is shown as SEQ ID No. 1. However, the present invention encompasses amino acid sequences encoding other members from the PDEXV family which would include amino acid sequences having at least 60% identity (more preferably at least 75% identity) to that specific amino acid sequences.

Polypeptides of the present invention also include fragments of the presented amino acid sequence and variants thereof. Suitable fragments will be at least 5, e.g. at least 10, 12, 15 or 20 amino acids in size.

Polypeptides of the present invention may also be modified to contain one or more (e.g. at least 2, 3, 5, or 10) substitutions, deletions or insertions, including conserved substitutions. These aspects are discussed in a later section.

Nucleotide Sequence of the Present Invention

The term "nucleotide sequence" as used herein refers to an oligonucleotide sequence or polynucleotide sequence, and variants, homologues, fragments and derivatives thereof (such as portions thereof). The nucleotide sequence may be DNA or RNA which may be of genomic or synthetic or recombinant origin which may be double-stranded or single-stranded whether representing the sense or antisense strand.

Preferably, the term "nucleotide sequence" means DNA.

More preferably, the term "nucleotide sequence" means DNA prepared by use of recombinant DNA techniques (i.e. recombinant DNA).

In a preferred embodiment, the nucleotide sequence per se of the present invention does not cover the native nucleotide coding sequence according to the present invention in its natural environment when it is under the control of its native promoter which is also in its natural environment. For ease of reference, we have called this preferred embodiment the "non-native nucleotide sequence".

The nucleotide sequences of the present invention may include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the nucleotide sequences described herein may be modified by any method available in the art. Such modifications may be carried out in to enhance the in vivo activity or life span of nucleotide sequences of the present invention.

The present invention also encompasses nucleotide sequences that are complementary to the sequences presented herein, or any derivative, fragment or derivative thereof. If the sequence is complementary to a fragment thereof then that sequence can be used a probe to identify similar coding sequences in other organisms etc.

The present invention also encompasses nucleotide sequences that are capable of hybridising to the sequences presented herein, or any derivative, fragment or derivative thereof.

The present invention also encompasses nucleotide sequences that are capable of hybridising to the sequences that are complementary to the sequences presented herein, or any derivative, fragment or derivative thereof.

The term "variant" also encompasses sequences that are complementary to sequences that are capable of hybridising to the nucleotide sequences presented herein.

Preferably, the term "variant" encompasses sequences that are complementary to sequences that are capable of hydridising under stringent conditions (e.g. 65° C. and 0.1×SSC {1×SSC=0.15 M NaCl, 0.015 $Na_3$ citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 65° C. and 0.1× SSC).

Exemplary nucleic acids can alternatively be characterised as those nucleotide sequences which encode a PDEXV protein and hybridise to the DNA sequence shown in the attached sequence listings. Preferred are such sequences encoding PDEXV which hybridise under high-stringency conditions to the sequence shown in the attached sequence listings or the complement thereof.

Advantageously, the invention provides nucleic acid sequences which are capable of hybridising, under stringent conditions, to a fragment of the sequence shown in the attached sequence listings or the complement thereof. Preferably, the fragment is between 15 and 50 bases in length. Advantageously, it is about 25 bases in length.

The terms "variant", "homologue" or "fragment" in relation to the nucleotide sequence coding for the preferred enzyme of the present invention include any substitution of, variation of, modification of, replacement of, deletion of or addition of one (or more) nucleic acid from or to the sequence providing the resultant nucleotide sequence codes for or is capable of coding for an enzyme having PDEXV activity, preferably being at least as biologically active as the enzyme encoded by the sequences shown in the attached sequence listings. In particular, the term "homologue" covers homology with respect to structure and/or function providing the resultant nucleotide sequence codes for or is capable of coding for an enzyme having PDEXV activity. With respect to sequence homology, preferably there is at least 75%, more preferably at least 85%, more preferably at least 90% homology to a nucleotide sequence coding for the amino acid sequence shown as SEQ ID No. 1. More preferably there is at least 95%, more preferably at least 98% homology to a nucleotide sequence coding for the amino acid sequence shown as SEQ ID No. 1. Preferably, with respect to sequence homology, preferably there is at least 75%, more preferably at least 85%, more preferably at least 90% homology to the sequence shown as SEQ ID No. 2. More preferably there is at least 95%, more preferably at least 98%, homology to the sequence shown as SEQ ID No. 2.

Preferably, the variant, homologue or fragment of the present invention comprises a nucleotide sequence that encodes for at least 25 contiguous amino acids, preferably at least 45 contiguous amino acids, preferably at least 65 contiguous amino acids, preferably at least 85 contiguous amino acids, preferably at least 105 contiguous amino acids, preferably at least 125 contiguous amino acids, preferably at least 145 contiguous amino acids, preferably at least 165 contiguous amino acids, preferably at least 185 contiguous amino acids, of the following N terminal sequence:

```
MLKQARRPLFRNVLSATQWKKVKITRLVQISGASLAEKQEKHQDFLIQRQTKTKDRRFND    (SEQ ID NO:7)

EIDKLTGYKTKSLLCMPIRSSDGEIIGVAQAINKIPEGAPFTEDDEKVMQMYLPFCGIAI

SNAQLFAASRKEYERSRALLEVVNDLFEEQTDLEKIVKKIMHRAQTLLKCERCSVLLLED

IESPVVKFTKSFEL
```

An example of a nucleotide sequence encoding an example of such a suitable N terminal sequence is presented below:

```
GGTCCGAGATGCTGAAGCAGGCAAGAAGACCTTTATTCAGAAATGTGCTCAGTGCC    (SEQ ID NO:8)

ACAC

AGTGGAAAAAGGTGAAAATCACAAGACTGGTCCAAATCTCTGGGGCCTCTTTGGCTG

AAA

AACAGGAAAAGCACCAGGATTTTCTTATACAGAGGCAAACAAAAACAAAGGATCGAC

GAT

TCAATGATGAAATCGACAAGCTGACTGGATACAAGACAAAATCATTATTGTGCATGCC

TA

TCCGAAGCAGTGATGGTGAGATTATTGGTGTGGCCCAAGCGATAAATAAGATTCCTG

AAG

GAGCTCCATTTACTGAAGATGATGAAAAAGTTATGCAGATGTATCTTCCATTTTGTGG

AA

TCGCCATATCTAACGCTCAGCTCTTTGCTGCCTCAAGGAAAGAATATGAAAGAAGCA

GAG

CTT
```

As indicated, the present invention relates to a DNA sequence (preferably a cDNA sequence) encoding PDEXV. In particular, the present invention relates to cDNA sequences encoding PDEXV.

The present invention also relates to DNA segments comprising the DNA sequence of the sequences shown in the attached sequence listings or allelic variations of such sequences.

The present invention also relates to polypeptides produced by expression in a host cell into which has been incorporated the foregoing DNA sequences or allelic variations thereof.

The present invention also relates provides DNA comprising the DNA sequence shown in the attached sequence listings or an allelic variation thereof.

The present invention also relates to non-native DNA comprising the DNA sequence shown in the attached sequence listings or an allelic variation thereof.

A highly preferred aspect of the present invention relates to recombinant DNA comprising the DNA sequence shown in the attached sequence listings or an allelic variation thereof.

Polynucleotides of the present invention include nucleotide acid sequences encoding the polypeptides of the present invention. It will appreciated that a range of different polynucleotides encode a given amino acid sequence as a consequence of the degeneracy of the genetic code.

By knowledge of the amino acid sequences set out herein it is possible to devise partial and full-length nucleic acid sequences such as cDNA and/or genomic clones that encode the polypeptides of the present invention. For example, polynucleotides of the present invention may be obtained using degenerate PCR which will use primers designed to target sequences encoding the amino acid sequences presented herein. The primers will typically contain multiple degenerate positions. However, to minimise degeneracy, sequences will be chosen that encode regions of the amino acid sequences presented herein containing amino acids such as methionine which are coded for by only one triplet. In addition, sequences will be chosen to take into account codon usage in the organism whose nucleic acid is used as the template DNA for the PCR procedure. PCR will be used at stringency conditions lower than those used for cloning sequences with single sequence (non-degenerate) primers against known sequences.

Nucleic acid sequences obtained by PCR that encode polypeptide fragments of the present invention may then be used to obtain larger sequences using hybridisation library screening techniques. For example a PCR clone may be labelled with radioactive atoms and used to screen a cDNA or genomic library from other species, preferably other mammalian species. Hybridisation conditions will typically be conditions of medium to high stringency (for example 0.03M sodium chloride and 0.03M sodium citrate at from about 50° C. to about 60° C.).

Degenerate nucleic acid probes encoding all or part of the amino acid sequence may also be used to probe cDNA and/or genomic libraries from other species, preferably other mammalian species. However, it is preferred to carry out PCR techniques initially to obtain a single sequence for use in further screening procedures.

In accordance with the present invention, PDEXV polynucleotide sequences which encode PDEXV, fragments of the polypeptide, fusion proteins or functional equivalents thereof, may be used to generate recombinant DNA molecules that direct the expression of PDEXV in appropriate host cells. Due to the inherent degeneracy of the genetic code, other DNA sequences which encode substantially the same or a functionally equivalent amino acid sequence, may be used to clone and express PDEXV. As will be understood by those of skill in the art, it may be advantageous to produce PDE-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of PDEXV expression or to produce recombinant RNA transcripts having desirable properties, such as a longer half-life, than transcripts produced from naturally occurring sequence.

Polynucleotide sequences of the present invention obtained using the techniques described above may be used to obtain further homologous sequences and variants using the techniques described above. They may also be modified for use in expressing the polypeptides of the present invention in a variety of host cells systems, for example to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Altered PDEXV polynucleotide sequences which may be used in accordance with the invention include deletions, insertions or substitutions of different nucleotide residues resulting in a polynucleotide that encodes the same or a functionally equivalent PDE. The protein may also have deletions, insertions or substitutions of amino acid residues which produce a silent change and result in a functionally equivalent PDE. Deliberate amino acid substitutions may be made on the basis of similarity in polarity, charge, solubility, hydrophobicity, hydrophilicity, and/or the amphipathic nature of the residues as long as the biological activity of PDE is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Included within the scope of the present invention are alleles of PDE. As used herein, an "allele" or "allelic sequence" is an alternative form of PDE. Alleles result from a mutation, i.e., a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention may be engineered in order to alter a PDE coding sequence for a variety of reasons, including but not limited to, alterations which modify the cloning, processing and/or expression of the gene product. For example, mutations may be introduced using techniques which are well known in the art, e.g., site-directed mutagenesis to insert new restriction sites, to alter glycosylation patterns or to change codon preference.

Polynucleotides of the present invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the present invention as used herein.

Polynucleotides or primers of the present invention may carry a revealing label. Suitable labels include radioisotopes such as $^{32}P$ or $^{35}S$, enzyme labels, or other protein labels such as biotin. Such labels may be added to polynucleotides or primers of the present invention and may be detected using by techniques known per se.

Polynucleotides such as a DNA polynucleotide and primers according to the present invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15–30 nucleotides) to a region of the nucleotide sequence which it is desired to clone, bringing the primers into contact with mRNA or cDNA obtained from a fungal, plant or prokaryotic cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

As mentioned earlier, the present invention also relates to nucleotide sequences that are capable of hybridising to all or part of the sequence shown in the attached sequence listings or an allelic variation thereof. These nucleotide sequences may be used in anti-sense techniques to modify PDEXV expression. Alternatively, these sequences (or portions thereof) can be used as a probe, or for amplifying all or part of such sequence when used as a polymerase chain reaction primer.

In addition to the recombinant DNA sequences, genomic sequences are also of utility in the context of drug discovery. It may be valuable to inhibit the mRNA transcription of a particular isoform rather than to inhibit its translated protein. This may be true with PDEXV, if there are splice variants and wherein those different splice variants may be transcribed from different promoters. There is precedent for multiple promoters directing the transcription of a mouse brain 2',3'-cyclic-nucleotide 3' phosphodiesterase (Kurihara T et al., Biochem. Biophys. Res. Comm. 170:1074 [1990]).

Another utility of the invention is that the DNA sequences, once known, give the information needed to design assays to specifically detect isoenzymes or splice variants. Isozyme-specific PCR primer pairs are but one example of an assay that depends completely on the knowledge of the specific DNA sequence of the isozyme or splice variant. Such an assay allows detection of mRNA for the isozyme to access the tissue distribution and biological relevance of each isozyme to a particular disease state. It also allows identification of cell lines that may naturally express only one isozyme—a discovery that might obviate the need to express recombinant genes. If specific PDEXV isozymes are shown to associated with a particular disease state, the invention would be valuable in the design of diagnostic assays to detect the presence of isozyme mRNA.

An abnormal level of nucleotide sequences encoding a PDEXV in a biological sample may reflect a chromosomal aberration, such as a nucleic acid deletion or mutation. Accordingly, nucleotide sequences encoding a PDEXV provide the basis for probes which can be used diagnostically to detect chromosomal aberrations such as deletions, mutations or chromosomal translocations in the gene encoding PDE. PDEXV gene expression may be altered in such disease states or there may be a chromosomal aberration present in the region of the gene encoding a PDEXV.

In an alternative embodiment of the invention, the coding sequence of PDE could be synthesized, in whole or in part, using chemical methods well known in the art (see Caruthers M H et al (1980) Nuc Acids Res Symp Ser 215–23, Horn T et al (1980) Nuc Acids Res Symp Ser 225–232).

Naturally Occurring

As used herein "naturally occurring" refers to a PDEXV with an amino acid sequence found in nature.

Isolated/Purified

As used herein, the terms "isolated" and "purified" refer to molecules, either nucleic or amino acid sequences, that are removed from their natural environment and isolated or separated from at least one other component with which they are naturally associated.

Biologically Active

As used herein "biologically active" refers to a PDEXV according to the present invention—such as a recombinant PDEXV—having a similar structural function (but not necessarily to the same degree), and/or similar regulatory function (but not necessarily to the same degree), and/or similar biochemical function (but not necessarily to the same degree) and/or immunological activity (but not necessarily to the same degree) of the naturally occurring PDEXV. Specifically, a PDEXV of the present invention has the ability to hydrolyse a cyclic nucleotide, which is one of the characteristic activities of the PDE enzyme of the present invention.

Immunological Activity

As used herein, "immunological activity" is defined as the capability of the natural, recombinant or synthetic PDEXV or any oligopeptide thereof, to induce a specific immune response in appropriate animals or cells and to bind with specific antibodies.

Derivative

The term "derivative" as used herein in relation to the amino acid sequence includes chemical modification of a PDEXV. Illustrative of such modifications would be replacement of hydrogen by an alkyl, acyl, or amino group.

Deletion

As used herein a "deletion" is defined as a change in either nucleotide or amino acid sequence in which one or more nucleotides or amino acid residues, respectively, are absent.

Insertion/Addition

As used herein an "insertion" or "addition" is a change in a nucleotide or amino acid sequence which has resulted in the addition of one or more nucleotides or amino acid residues, respectively, as compared to the naturally occurring PDE.

Substitution

As used herein "substitution" results from the replacement of one or more nucleotides or amino acids by different nucleotides or amino acids, respectively.

Homologue

The term "homologue" with respect to the nucleotide sequence of the present invention and the amino acid sequence of the present invention may be synonymous with allelic variations of the sequences.

In particular, the term "homology" as used herein may be equated with the term "identity". Here, sequence homology with respect to the nucleotide sequence of the present invention and the amino acid sequence of the present invention can be determined by a simple "eyeball" comparison (i.e. a strict comparison) of any one or more of the sequences with another sequence to see if that other sequence has at least 75% identity to the sequence(s). Relative sequence homology (i.e. sequence identity) can also be determined by commercially available computer programs that can calculate % homology between two or more sequences. A typical example of such a computer program is CLUSTAL.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is –12 for a gap and –4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for off-line and on-line searching (see Ausubel et al., 1999 ibid, pages 7–58 to 7–60). However, for some applications it is preferred to use the GCG Bestfit program.

Although the final % homology can be measured in terms of identity, in some cases, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

As indicated, for some applications, sequence homology (or identity) may be determined using any suitable homology algorithm, using for example default parameters. For a discussion of basic issues in similarity searching of sequence databases, see Altschul et al (1994) Nature Genetics 6:119–129. For some applications, the BLAST algorithm is employed, with parameters set to default values. The BLAST algorithm is described in detail at the NCBI website. Advantageously, "substantial homology" when assessed by BLAST equates to sequences which match with an EXPECT value of at least about 7, preferably at least about 9 and most preferably 10 or more. The default threshold for EXPECT in BLAST searching is usually 10.

Should Gap Penalties be used when determining sequence identity, then preferably the following parameters are used:

| FOR BLAST | | | |
|---|---|---|---|
| GAP OPEN | 0 | | |
| GAP EXTENSION | 0 | | |
| FOR CLUSTAL | DNA | PROTEIN | |
| WORD SIZE | 2 | 1 | K triple |
| GAP PENALTY | 10 | 10 | |
| GAP EXTENSION | 0.1 | 0.1 | |

Other computer program methods to determine identify and similarity between the two sequences include but are not limited to the GCG program package (Devereux et al 1984 Nucleic Acids Research 12: 387 and FASTA (Atschul et al 1990 J Molec Biol 403–410).

Polypeptide Variants and Derivatives

The terms "variant" or "derivative" in relation to the amino acid sequences of the present invention includes any substitution of, variation of, modification of, replacement of, deletion of or addition of one (or more) amino acids from or to the sequence providing the resultant amino acid sequence has PDE activity, preferably having at least the same activity as the polypeptide presented in the sequence listings.

The sequences of the present invention may be modified for use in the present invention. Typically, modifications are made that maintain the PDE activity of the sequence. Amino acid substitutions may be made, for example from 1, 2 or 3 to 10, 20 or 30 substitutions provided that the modified sequence retains the PDE activity. Amino acid substitutions may include the use of non-naturally occurring analogues, for example to increase blood plasma half-life of a therapeutically administered polypeptide.

Conservative substitutions may be made, for example according to the Table below. Amino acids in the same block in the second column and preferably in the same line in the third column may be substituted for each other:

| ALIPHATIC | Non-polar | GAP |
| | | ILV |
| | Polar - uncharged | CSTM |
| | | NQ |
| | Polar - charged | DE |
| | | KR |
| AROMATIC | | HFWY |

As indicated above, proteins of the invention are typically made by recombinant means, for example as described herein, and/or by using synthetic means using techniques well known to skilled persons such as solid phase synthesis. Variants and derivatives of such sequences include fusion proteins, wherein the fusion proteins comprise at least the amino acid sequence of the present invention being linked (directly or indirectly) to another amino acid sequence. These other amino acid sequences—which are sometimes referred to as fusion protein partners—will typically impart a favourable functionality—such as to aid extraction and purification of the amino acid sequence of the present invention. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of the present invention so as to allow removal of the latter. Preferably the fusion protein partner will not hinder the function of the protein of the present invention.

Polynucleotide Variants and Derivatives

The terms "variant" or "derivative" in relation to the nucleotide sequence of the present invention include any substitution of, variation of, modification of, replacement of, deletion of or addition of one (or more) nucleic acid from or to the sequence providing the resultant nucleotide sequence codes for a polypeptide having PDE activity, preferably having at least the same activity as sequences presented in the sequence listings.

As indicated above, with respect to sequence homology, preferably there is at least 75%, more preferably at least 85%, more preferably at least 90% homology to the sequences shown in the sequence listing herein. More preferably there is at least 95%, more preferably at least 98%, homology. Nucleotide homology comparisons may be conducted as described above. For some applications, a preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

As used herein, the terms "variant", "homologue", "fragment" and "derivative" embrace allelic variations of the sequences.

The term "variant" also encompasses sequences that are complementary to sequences that are capable of hydridising to the nucleotide sequences presented herein.

Hybridisation

The term "hybridisation" as used herein shall include "the process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach C W and G S Dveksler (1995, PCR Primer, a Laboratory Manual, Cold Spring Harbor Press, Plainview N.Y.).

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na+ at 65–68° C.

Maximum stringency typically occurs at about Tm−5° C. (5° C. below the Tm of the probe).

High stringency at about 5° C. to 10° C. below the Tm of the probe. High stringency conditions can be provided, for example, by hybridisation in an aqueous solution containing 6×SSC, 5× Denhardt's, 1% SDS (sodium dodecyl sulphate), 0.1 Na+ pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1×SSC, 0.1% SDS.

Moderate, or intermediate, stringency typically occurs at about 10° C to 20° C. below the Tm of the probe.

Low stringency typically occurs at about 20° C. to 25° C. below the Tm of the probe.

As will be understood by those of skill in the art, a maximum stringency hybridisation can be used to identify or detect identical polynucleotide sequences while an intermediate (or low) stringency hybridisation can be used to identify or detect similar or related polynucleotide sequences.

Moderate stringency refers to conditions equivalent to hybridisation in the above described solution but at about 60–62° C. In that case the final wash is performed at the hybridisation temperature in 1×SSC, 0.1% SDS.

Low stringency refers to conditions equivalent to hybridisation in the above described solution at about 50–52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g. Sambrook, et al., eds. (1989) Molecular Cloning: A Laboratory Manual, Cold Spring Harbor Laboratory Press, New York or Ausubel, et al., eds. (1990) Current Protocols in Molecular Biology, John Wiley & Sons, Inc.). Optimal hybridisation conditions have to be determined empirically, as the length and the GC content of the probe also play a role.

Polynucleotides of the invention capable of selectively hybridising to the nucleotide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridisable" means that the polynucleotide used as a probe is used under conditions where a target polynucleotide of the invention is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

In a preferred aspect, the present invention covers nucleotide sequences that can hybridise to any one or more of the nucleotide sequences of the present invention under stringent conditions (e.g. 65° C. and 0.1×SSC {1×SSC=0.15 M NaCl, 0.015 M $Na_3$ Citrate pH 7.0).

Where the polynucleotide of the present invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of the sequence in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Regulatory Sequences

Preferably, the polynucleotide of the present invention is operably linked to a regulatory sequence which is capable of providing for the expression of the coding sequence, such as by the chosen host cell. By way of example, the present invention covers a vector comprising the polynucleotide of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the polynucleotide encoding the polypeptide of the present invention may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the polypeptide of the present invention Preferably, the nucleotide sequence of the present invention may be operably linked to at least a promoter.

Aside from the promoter native to the gene encoding the polypeptide of the present invention, other promoters may be used to direct expression of the polypeptide of the present invention. The promoter may be selected for its efficiency in directing the expression of the polypeptide of the present invention in the desired expression host.

In another embodiment, a constitutive promoter may be selected to direct the expression of the desired polypeptide of the present invention. Such an expression construct may provide additional advantages since it circumvents the need to culture the expression hosts on a medium containing an inducing substrate.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the nucleotide sequence of the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat Gene 217 [1987] 217–225; and Dawson Plant Mol. Biol. 23 [1993] 97).

Secretion

Often, it is desirable for the polypeptide of the present invention to be secreted from the expression host into the culture medium from where the polypeptide of the present invention may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces* and *Kluyveromyces*) or the α-amylase gene (*Bacillus*).

Constructs

The term "construct"—which is synonymous with terms such as "conjugate", "cassette" and "hybrid"—includes the nucleotide sequence according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In each case, the terms do not cover the natural combination of the nucleotide sequence coding for the protein ordinarily associated with the wild type gene promoter and when they are both in their natural environment.

The construct may even contain or express a marker which allows for the selection of the genetic construct in, for example, a bacterium, preferably of the genus *Bacillus*, such as *Bacillus subtilis*, or plants into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

Preferably the construct of the present invention comprises at least the nucleotide sequence of the present invention operably linked to a promoter.

Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the species or may be of a different species. If the construct is capable of being transferred from one species to another—such as from an *E.coli* plasmid to a bacterium, such as of the genus *Bacillus*, then the transformation vector is sometimes called a "shuttle vector". It may even be a construct capable of being transferred from an *E.coli* plasmid to an *Agrobacterium* to a plant.

The vectors of the present invention may be transformed into a suitable host cell as described below to provide for expression of a polypeptide of the present invention. Thus, in a further aspect the invention provides a process for preparing polypeptides according to the present invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter.

The vectors of the present invention may contain one or more selectable marker genes. The most suitable selection systems for industrial micro-organisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in yeast, but not in filamentous fungi), the ampicillin resistance gene (*E. coli*), the neomycin resistance gene (*Bacillus*) and the *E.coli uidA* gene, coding for β-glucuronidase (GUS).

Vectors may be used in vitro, for example for the production of RNA or used to transfect or transform a host cell.

Thus, polynucleotides of the present invention can be incorporated into a recombinant vector (typically a replicable vector), for example a cloning or expression vector. The vector may be used to replicate the nucleic acid in a compatible host cell. Thus in a further embodiment, the invention provides a method of making polynucleotides of the present invention by introducing a polynucleotide of the present invention into a replicable vector, introducing the vector into a compatible host cell, and growing the host cell under conditions which bring about replication of the vector. The vector may be recovered from the host cell. Suitable host cells are described below in connection with expression vectors.

The present invention also relates to the use of genetically engineered host cells expressing a PDEXV or variant, homologue, fragment or derivative thereof in screening methods for the identification of inhibitors and antagonists of the PDEXV that would modulate phosphodiesterase activity thereby modulating cyclic nucleotide levels. Such genetically engineered host cells could be used to screen peptide libraries or organic molecules capable of modulating PDEXV activity. Antagonists and inhibitors of PDEXV, such as antibodies, peptides or small organic molecules will provide the basis for pharmaceutical compositions for the treatment of diseases associated with, for example, PDEXV. Such inhibitors or antagonists can be administered alone or in combination with other therapeutics for the treatment of such diseases.

The present invention also relates to expression vectors and host cells comprising polynucleotide sequences encoding PDEXV or variant, homologue, fragment or derivative thereof for the in vivo or in vitro production of PDEXV protein or to screen for agents that can affect PDEXV expression or activity.

Tissue

The term "tissue" as used herein includes tissue per se and organ.

Host Cells

The term "host cell"—in relation to the present invention includes any cell that could comprise the nucleotide sequence coding for the recombinant protein according to the present invention and/or products obtained therefrom, wherein a promoter can allow expression of the nucleotide sequence according to the present invention when present in the host cell.

Thus, a further embodiment of the present invention provides host cells transformed or transfected with a polynucleotide of the present invention. Preferably said polynucleotide is carried in a vector for the replication and expression of said polynucleotides. The cells will be chosen to be compatible with the said vector and may for example be prokaryotic (for example bacterial), fungal, yeast or plant cells.

The gram-negative bacterium E. coli is widely used as a host for heterologous gene expression. However, large amounts of heterologous protein tend to accumulate inside the cell. Subsequent purification of the desired protein from the bulk of E. coli intracellular proteins can sometimes be difficult.

In contrast to E. coli, bacteria from the genus Bacillus are very suitable as heterologous hosts because of their capability to secrete proteins into the culture medium. Other bacteria suitable as hosts are those from the genera Streptomyces and Pseudomonas.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as Aspergillus species (such as those described in EP-A-0184438 and EP-A-0284603) and Trichoderma species; bacteria such as Bacillus species (such as those described in EP-A-0134048 and EP-A-0253455), Streptomyces species and Pseudomonas species; and yeasts such as Kluyveromyces species (such as those described in EP-A-0096430 and EP-A-0301670) and Saccharomyces species. By way of example, typical expression hosts may be selected from Aspergillus niger, Aspergillus niger var. tubigenis, Aspergillus niger var. awamori, Aspergillus aculeatis, Aspergillus nidulans, Aspergillus orvzae, Trichoderma reesei, Bacillus subtilis, Bacillus licheniformis, Bacillus amyloliquefaciens, Kluyveromyces lactis and Saccharomyces cerevisiae.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism that could comprise the nucleotide sequence coding for the recombinant protein according to the present invention and/or products obtained therefrom, wherein a promoter can allow expression of the nucleotide sequence according to the present invention when present in the organism. Examples of organisms may include a fungus, yeast or a plant.

The term "transgenic organism" in relation to the present invention includes any organism that comprises the nucleotide sequence coding for the protein according to the present invention and/or products obtained therefrom, wherein the promoter can allow expression of the nucleotide sequence according to the present invention within the organism. Preferably the nucleotide sequence is incorporated in the genome of the organism.

The term "transgenic organism" does not cover the native nucleotide coding sequence according to the present invention in its natural environment when it is under the control of its native promoter which is also in its natural environment. In addition, the present invention does not cover the native protein according to the present invention when it is in its natural environment and when it has been expressed by its native nucleotide coding sequence which is also in its natural environment and when that nucleotide sequence is under the control of its native promoter which is also in its natural environment.

Therefore, the transgenic organism of the present invention includes an organism comprising any one of, or combinations of, the nucleotide sequence coding for the amino acid sequence according to the present invention, constructs according to the present invention (including combinations thereof), vectors according to the present invention, plasmids according to the present invention, cells according to the present invention, tissues according to the present invention or the products thereof. The transformed cell or organism could prepare acceptable quantities of the desired compound which would be easily retrievable from, the cell or organism.

Transformation of Host Cells/Host Organisms

As indicated earlier, the host organism can be a prokaryotic or a eukaryotic organism. Examples of suitable prokaryotic hosts include E. coli and Bacillus subtilis. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species Saccharomyces cerevisiae has a long history of industrial use, including its use for heterologous gene expression. Expression of heterologous genes in Saccharomyces cerevisiae has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons Saccharomyces cerevisiae is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of Saccharomyces cerevisiae.

A review of the principles of heterologous gene expression in Saccharomyces cerevisiae and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27). Further teachings on plant transformation may be found in EP-A-0449375.

Thus, the present invention also provides a method of transforming a host cell with a nucleotide sequence shown in the attached sequence listings or a derivative, homologue, variant or fragment thereof.

Host cells transformed with a PDE nucleotide coding sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing PDE coding sequences can be designed with signal sequences which direct secretion of PDE coding sequences through a particular prokaryotic or eukaryotic cell membrane. Other recombinant constructions may join PDE coding sequence to nucleotide sequence encoding a polypeptide domain which will facilitate purification of soluble proteins (Kroll D J et al (1993) DNA Cell Biol 12:441–53, see also above discussion of vectors containing fusion proteins).

Production of the Polypeptide

According to the present invention, the production of the polypeptide of the present invention can be effected by the culturing of, for example, microbial expression hosts, which have been transformed with one or more polynucleotides of the present invention, in a conventional nutrient fermentation medium. The selection of the appropriate medium may be based on the choice of expression hosts and/or based on the regulatory requirements of the expression construct. Such media are well-known to those skilled in the art. The medium may, if desired, contain additional components favouring the transformed expression hosts over other potentially contaminating micro-organisms.

Thus, the present invention also provides a method for producing a polypeptide having PDEXV activity, the method comprising the steps of a) transforming a host cell with a nucleotide sequence shown in the attached sequence listings or a derivative, homologue, variant or fragment thereof; and b) culturing the transformed host cell under conditions suitable for the expression of said polypeptide.

The present invention also provides a method for producing a polypeptide having PDEXV activity, the method comprising the steps of a) culturing a host cell that has been transformed with a nucleotide sequence shown in the attached sequence listings or a derivative, homologue, variant or fragment thereof under conditions suitable for the expression of said polypeptide; and b) recovering said polypeptide from the host cell culture.

The present invention also provides a method for producing a polypeptide having PDEXV activity, the method comprising the steps of a) transforming a host cell with a nucleotide sequence shown in the attached sequence listings or a derivative, homologue, variant or fragment thereof; b) culturing the transformed host cell under conditions suitable for the expression of said polypeptide; and c) recovering said polypeptide from the host cell culture.

Ribozymes

Ribozymes are enzymatic RNA molecules capable of catalysing the specific cleavage of RNA. The mechanism of ribozyme action involves sequence specific hybridisation of the ribozyme molecule to complementary target RNA, followed by a endonucleolytic cleavage. Within the scope of the invention are engineered hammerhead motif ribozyme molecules that specifically and efficiently catalyse endonucleolytic cleavage of PDE RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridisation with complementary oligonucleotides using ribonuclease protection assays.

Both antisense RNA and DNA molecules and ribozymes of the invention may be prepared by any method known in the art for the synthesis of RNA molecules. These include techniques for chemically synthesising oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

Detection

The presence of the PDE polynucleotide coding sequence can be detected by DNA-DNA or DNA-RNA hybridisation or amplification using probes, portions or fragments of the sequence presented in the attached sequence listings. Nucleic acid amplification based assays involve the use of oligonucleotides or oligomers based on the PDE coding sequence to detect transformants containing PDE DNA or RNA. As used herein "oligonucleotides" or "oligomers" may refer to a nucleic acid sequence of at least about 10 nucleotides and as many as about 60 nucleotides, preferably about 15 to 30 nucleotides, and more preferably about 20–25 nucleotides which can be used as a probe or amplimer. Preferably, oligonucleotides are derived from the 3' region of the nucleotide sequence shown in the attached sequence listings.

A variety of protocols for detecting and measuring the expression of PDE polypeptide, such as by using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes on PDE polypeptides is preferred, but a competitive binding assay may be employed. These and other assays are described, among other places, in Hampton R et al (1990, Serological Methods, A Laboratory Manual, APS Press, St Paul Minn.) and Maddox D E et al (1983, J Exp Med 15 8:121 1).

A wide variety of labels and conjugation techniques are known by those skilled in the art and can be used in various nucleic and amino acid assays. Means for producing labelled hybridisation or PCR probes for detecting PDE polynucleotide sequences include oligolabelling, nick translation, end-labelling or PCR amplification using a labelled nucleotide. Alternatively, the PDE coding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labelled nucleotides.

A number of companies such as Pharmacia Biotech (Piscataway, N.J.), Promega (Madison, Wis.), and US Biochemical Corp (Cleveland, Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567.

Additional methods to quantify the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantification of multiple samples may be speeded up by running the assay in an ELISA format where the oligomer of interest is presented in various dilutions and a spectrophotometric or calorimetric response gives rapid quantification.

Although the presence/absence of marker gene expression suggests that the gene of interest is also present, its presence and expression should be confirmed. For example, if the PDE coding sequence is inserted within a marker gene sequence, recombinant cells containing PDE coding regions can be identified by the absence of marker gene function. Alternatively, a marker gene can be placed in tandem with a PDE coding sequence under the control of a single promoter. Expression of the marker gene in response to induction or selection usually indicates expression of PDE as well.

Alternatively, host cells which contain the coding sequence for PDE and express PDE coding regions may be identified by a variety of procedures known to those of skill in the art. These procedures include, but are not limited to, DNA-DNA or DNA-RNA hybridisation and protein bioassay or immunoassay techniques which include membrane-based, solution-based, or chip-based technologies for the detection and/or quantification of the nucleic acid or protein.

Antibodies

The amino acid sequence of the present invention can also be used to generate antibodies—such as by use of standard techniques—against the amino acid sequence.

Procedures well known in the art may be used for the production of antibodies to PDEXV polypeptides. Such antibodies include, but are not limited to, polyclonal, monoclonal, chimeric, single chain, Fab fragments and fragments produced by a Fab expression library. Neutralising antibodies, i.e., those which inhibit biological activity of PDE polypeptides, are especially preferred for diagnostics and therapeutics.

For the production of antibodies, various hosts including goats, rabbits, rats, mice, etc. may be immunised by injection with the inhibitor or any portion, variant, homologue, fragment or derivative thereof or oligopeptide which retains immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (*Bacilli Calmette-Guerin*) and *Corynebacterium parvum* are potentially useful human adjuvants which may be employed.

Monoclonal antibodies to the amino acid sequence may be even prepared using any technique which provides for the production of antibody molecules by continuous cell lines in culture. These include, but are not limited to, the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) Monoclonal Antibodies and Cancer Therapy, Alan R Liss Inc, pp 77–96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,779) can be adapted to produce inhibitor specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for PDEXV may also be generated. For example, such fragments include, but are not limited to, the F(ab')$_2$ fragments which can be produced by pepsin digestion of the antibody molecule and the Fab fragments which can be generated by reducing the disulphide bridges of the F(ab')$_2$ fragments. Alternatively, Fab expression libraries may be constructed to allow rapid and easy identification of monoclonal Fab fragments with the desired specificity (Huse W D et al (1989) Science 256:1275–128 1).

An alternative technique involves screening phage display libraries where, for example the phage express scFv fragments on the surface of their coat with a large variety of complementarity determining regions (CDRs). This technique is well known in the art.

PDEXV-specific antibodies are useful for the diagnosis of conditions and diseases associated with expression of PDEXV polypeptide. A variety of protocols for competitive binding or immunoradiometric assays using either polyclonal or monoclonal antibodies with established specificities are well known in the art. Such immunoassays typically involve the formation of complexes between PDEXV polypeptides and its specific antibody (or similar PDEXV-binding molecule) and the measurement of complex formation. A two-site, monoclonal based immunoassay utilising monoclonal antibodies reactive to two non-interfering epitopes on a specific PDEXV protein is preferred, but a competitive binding assay may also be employed. These assays are described in Maddox D E et al (1983, J Exp Med 158:121 1).

Anti-PDEXV antibodies are useful for the diagnosis of inflammation, conditions associated with proliferation of haematopoietic cells and HIV infection or other disorders or diseases characterised by abnormal expression of a PDEXV. Diagnostic assays for a PDEXV include methods utilising the antibody and a label to detect a PDEXV polypeptide in human body fluids, cells, tissues or sections or extracts of such tissues. The polypeptides and antibodies of the present invention may be used with or without modification. Frequently, the polypeptides and antibodies will be labelled by joining them, either covalently or noncovalently, with a reporter molecule. A wide variety of reporter molecules are known to those of skill in the art.

Antibodies may be used in method of detecting polypeptides of the invention present in biological samples by a method which comprises: (a) providing an antibody of the invention; (b) incubating a biological sample with said antibody under conditions which allow for the formation of an antibody-antigen complex; and (c) determining whether antibody-antigen complex comprising said antibody is formed.

Depending on the circumstances, suitable samples may include extracts tissues such as brain, breast, ovary, lung, colon, pancreas, testes, liver, muscle and bone tissues or from neoplastic growths derived from such tissues.

Antibodies of the invention may be bound to a solid support and/or packaged into kits in a suitable container along with suitable reagents, controls, instructions and the like.

Assays/Identification Methods

The present invention also relates to an assay method for detecting the presence of PDEXV in cells (such as human cells) comprising: (a) performing a reverse transcriptase-polymerase chain reaction on RNA (such as total RNA) from such cells using a pair of polymerase chain reaction primers that are specific for PDEXV, as determined from the DNA sequence shown in the attached sequence listings or an allelic variation thereof; and (b) assaying the appearance of an appropriately sized PCR (polymerase chain reaction) fragment—such as by agarose gel electrophoresis.

The present invention also relates to a method of identifying agents (such as compounds, other substances or compositions comprising same) that affect (such as inhibit or otherwise modify) the activity of PDEXV and/or the expression thereof, the method comprising contacting PDEXV or the nucleotide sequence coding for same with the agent and then measuring the activity of PDEXV and/or the expression thereof.

The present invention also relates to a method of identifying agents (such as compounds, other substances or compositions comprising same) that selectively affect (such as inhibit or otherwise modify) the activity of PDEXV and/or the expression thereof, the method comprising contacting PDEXV or the nucleotide sequence coding for same with the agent and then measuring the activity of PDEXV and/or the expression thereof.

The present invention also relates to a method of identifying agents (such as compounds, other substances or compositions comprising same) that affect (such as inhibit or otherwise modify) the activity of PDEXV and/or the expression thereof, the method comprising measuring the activity of PDEXV and/or the expression thereof in the presence of the agent or after the addition of the agent in: (a) a cell line into which has been incorporated recombinant DNA comprising the DNA sequence shown in the attached sequence listings or an allelic variation thereof, or (b) a cell population or cell line that naturally selectively expresses PDEXV. Preferably, the activity of PDEXV is determined by the assay method described above.

The present invention also relates to a method of identifying agents (such as compounds, other substances or compositions comprising same) that selectively affect (such as inhibit or otherwise modify) the activity of PDEXV and/or the expression thereof, the method comprising measuring the activity of PDEXV and/or the expression thereof in the presence of the agent or after the addition of the agent in: (a) a cell line into which has been incorporated recombinant DNA comprising the DNA sequence shown in the attached sequence listings or an allelic variation thereof, or (b) a cell population or cell line that naturally selectively expresses PDEXV. Preferably, the activity of PDEXV is determined by the assay method described above.

The present invention also provides a method of screening an agent for modulation (preferably for specific modulation) of PDEXV (or a derivative, homologue, variant or fragment thereof) activity or the expression of the nucleotide sequence coding for same (including a derivative, homologue, variant or fragment thereof), the method comprising the steps of: a) providing a candidate agent; b) combining PDEXV (or the derivative, homologue, variant or fragment thereof) or the nucleotide sequence coding for same (or the derivative, homologue, variant or fragment thereof) with the candidate agent for a time sufficient to allow modulation under suitable conditions; and c) detecting modulation of the candidate agent to PDEXV (or the derivative, homologue, variant or fragment thereof) or the nucleotide sequence coding for same (or the derivative, homologue, variant or fragment thereof) in order to ascertain if the candidate agent modulates PDEXV (or the derivative, homologue, variant or fragment thereof) activity or the expression of the nucleotide sequence coding for same (or the derivative, homologue, variant or fragment thereof).

The present invention also provides a method of screening an agent for specific binding affinity with PDEXV (or a derivative, homologue, variant or fragment thereof) or the nucleotide sequence coding for same (including a derivative, homologue, variant or fragment thereof), the method comprising the steps of: a) providing a candidate agent; b) combining PDEXV (or the derivative, homologue, variant or fragment thereof) or the nucleotide sequence coding for same (or the derivative, homologue, variant or fragment thereof) with the candidate agent for a time sufficient to allow binding under suitable conditions; and c) detecting binding of the candidate agent to PDEXV (or the derivative, homologue, variant or fragment thereof) or the nucleotide sequence coding for same (or the derivative, homologue, variant or fragment thereof) in order to ascertain if the candidate agent binds to PDEXV (or the derivative, homologue, variant or fragment thereof) or the nucleotide sequence coding for same (or the derivative, homologue, variant or fragment thereof).

The present invention also provides a method of identifying an agent which is capable of modulating PDEXV, the method comprising the steps of: a) contacting the agent with PDEXV (or a derivative, homologue, variant or fragment thereof) or the nucleotide sequence coding for same (or the derivative, homologue, variant or fragment thereof), b) incubating the mixture of step a) with a cyclic nucleotide under conditions suitable for the hydrolysis of the cyclic nucleotide, c) measuring the amount of cyclic nucleotide hydrolysis, and d) comparing the amount of cyclic nucleotide hydrolysis of step c) with the amount of cyclic nucleotide hydrolysis obtained with PDEXV (or the derivative, homologue, variant or fragment thereof) or the nucleotide sequence coding for same (or the derivative, homologue, variant or fragment thereof) incubated without the compound, thereby determining whether the agent affects (such as stimulates or inhibits) cyclic nucleotide hydrolysis.

Thus, in certain embodiments of the present invention, PDEXV or a variant, homologue, fragment or derivative thereof and/or a cell line that expresses the PDEXV or variant, homologue, fragment or derivative thereof may be used to screen for antibodies, peptides, or other agent, such as organic or inorganic molecules, that act as modulators of phosphodiesterase activity or for the expression thereof, thereby identifying a therapeutic agent capable of modulating cyclic nucleotide levels. For example, anti-PDEXV antibodies capable of neutralising the activity of PDEXV may be used to inhibit PDEXV hydrolysis of cyclic nucleotides, thereby increasing their levels. Alternatively, screening of peptide libraries or organic libraries made by combinatorial chemistry with recombinantly expressed PDEXV or a variant, homologue, fragment or derivative thereof or cell lines expressing PDEXV or a variant, homologue, fragment or derivative thereof may be useful for identification of therapeutic agents that function by modulating PDEXV hydrolysis of cyclic nucleotides. Synthetic compounds, natural products, and other sources of potentially biologically active materials can be screened in a number of ways deemed to be routine to those of skill in the art. For example, nucleotide sequences encoding the N-terminal region of PDEXV may be expressed in a cell line which can be used for screening of allosteric modulators, either agonists or antagonists, of PDEXV activity. Alternatively, nucleotide sequences encoding the conserved catalytic domain of PDEXV can be expressed in cell lines and used to screen for inhibitors of cyclic nucleotide hydrolysis.

The ability of a test agent to interfere with PDEXV activity or cyclic nucleotide hydrolysis may be determined by measuring PDEXV levels or cyclic nucleotide levels (as disclosed in Smith et al 1993 Appl. Biochem. Biotechnol. 41:189–218). There are also commercially available immunoassay kits for the measurement of cAMP and cGMP (eg Amersham International, Arlington Heights, Ill. and DuPont, Boston, Mass.). The activity of PDEXV may also be monitored by measuring other responses such as phosphorylation or dephosphorylation of other proteins using conventional techniques developed for these purpose.

Accordingly, the present invention provides a method of identifying a compound which is capable of modulating the cyclic nucleotide phosphodiesterase activity of a PDEXV, or a variant, homologue, fragment or derivative thereof, comprising the steps of a) contacting the compound with a PDEXV, or a variant, homologue, fragment or derivative thereof; b) incubating the mixture of step a) with a cyclic nucleotide under conditions suitable for the hydrolysis of the cyclic nucleotide; c) measuring the amount of cyclic nucleotide hydrolysis; and d) comparing the amount of cyclic nucleotide hydrolysis of step c) with the amount of cyclic nucleotide hydrolysis obtained with the PDEXV, or a variant, homologue, fragment or derivative thereof, incubated without the compound, thereby determining whether the compound stimulates or inhibits cyclic nucleotide hydrolysis. In one embodiment of the method, the fragment may be from the N-terminal region of the PDEXV and provides a method to identify allosteric modulators of the PDEXV. In another embodiment of the present invention, the fragment may be from the carboxy terminal region of the PDEXV and provides a method to identify inhibitors of cyclic nucleotide hydrolysis.

A PDEXV polypeptide, its immunogenic fragments or oligopeptides thereof can be used for screening therapeutic compounds in any of a variety of drug screening techniques. The polypeptide employed in such a test may be free in solution, affixed to a solid support, borne on a cell surface, or located intracellularly. The abolition of activity or the formation of binding complexes between a PDEXV polypeptide and the agent being tested may be measured.

Accordingly, the present invention provides a method for screening one or a plurality of compounds for modulation (preferably specific modulation, such as specific binding affinity) of PDEXV or the expression thereof, or a portion thereof or variant, homologue, fragment or derivative thereof, comprising providing one or a plurality of compounds; combining a PDEXV or a nucleotide sequence coding for same or a portion thereof or variant, homologue, fragment or derivative thereof with the or each of a plurality of compounds for a time sufficient to allow modulation under suitable conditions; and detecting binding of a PDEXV, or portion thereof or variant, homologue, fragment or derivative thereof, to each of the plurality of compounds, thereby identifying the compound or compounds which modulate a PDEXV or a nucleotide sequence coding for same. In such an assay, the plurality of compounds may be produced by combinatorial chemistry techniques known to those of skill in the art.

Another technique for drug screening provides for high throughput screening of compounds having suitable binding affinity to the PDEXV polypeptides and is based upon the method described in detail in Geysen, European Patent Application 84/03564, published on Sep. 13, 1984. In summary, large numbers of different small peptide test compounds are synthesized on a solid substrate, such as plastic pins or some other surface. The peptide test compounds are reacted with PDEXV fragments and washed. A bound PDEXV is then detected—such as by appropriately adapting methods well known in the art. A purified PDEXV can also be coated directly onto plates for use in the aforementioned drug screening techniques. Alternatively, non-neutralising antibodies can be used to capture the peptide and immobilise it on a solid support.

This invention also contemplates the use of competitive drug screening assays in which neutralising antibodies capable of binding a PDEXV specifically compete with a test compound for binding a PDEXV. In this manner, the antibodies can be used to detect the presence of any peptide which shares one or more antigenic determinants with a PDEXV.

The assay method of the present invention may be a high throughput screen (HTS). In this regard, the teachings of WO 84/03564 may be adapted for the PDE of the present invention.

The teachings of U.S. Pat. No. 5,738,985 may be adapted for the assay method of the present invention.

Agents

The present invention also provides one or more agents identified by the assays methods and identification methods of the present invention.

The agent of the present invention can be, for example, an organic compound or an inorganic compound. The agent can be, for example, a nucleotide sequence that is anti-sense to all or part of the sequences shown in the attached sequence listings.

The invention further provides an agent of the present invention (or even a pharmaceutically acceptable salt thereof, or a pharmaceutically acceptable solvate thereof) or a pharmaceutical composition containing any of the foregoing, for use as a medicament.

The present invention also provides the use of an agent to affect PDEXV activity (such as to inhibit, modulate or agonise) in any one or more of the cardiovascular system, the corpus cavernosum, kidney, liver, skeletal muscle, testis, prostate.

Diagnostics

The present invention also provides a diagnostic composition for the detection of PDEXV polynucleotide sequences. The diagnostic composition may comprise any one of the sequences shown in the attached sequence listings or a variant, homologue, fragment or derivative thereof, or a sequence capable of hybridising to all or part of any one of the nucleotide sequence shown in the attached sequence listings or an allelic variation thereof.

In order to provide a basis for the diagnosis of disease, normal or standard values from a PDEXV polypeptide expression should be established. This is accomplished by combining body fluids or cell extracts taken from normal subjects, either animal or human, with antibody to a PDEXV polypeptide under conditions suitable for complex formation which are well known in the art. The amount of standard complex formation may be quantified by comparing it to a dilution series of positive controls where a known amount of antibody is combined with known concentrations of a purified PDEXV polypeptide. Then, standard values obtained from normal samples may be compared with values obtained from samples from subjects potentially affected by a disorder or disease related to a PDEXV polypeptide expression. Deviation between standard and subject values establishes the presence of the disease state.

A PDEXV polynucleotide, or any part thereof, may provide the basis for a diagnostic and/or a therapeutic compound. For diagnostic purposes, PDEXV polynucleotide sequences may be used to detect and quantify gene expression in conditions, disorders or diseases in which PDEXV activity may be implicated.

PDEXV encoding polynucleotide sequence may be used for the diagnosis of diseases resulting from expression of PDEXV. For example, polynucleotide sequences encoding PDEXV may be used in hybridisation or PCR assays of tissues from biopsies or autopsies or biological fluids, such as serum, synovial fluid or tumour biopsy, to detect abnormalities in PDEXV expression. The form of such qualitative or quantitative methods may include Southern or northern analysis, dot blot or other membrane-based technologies; PCR technologies; dip stick, pin or chip technologies; and ELISA or other multiple sample format technologies. All of these techniques are well known in the art and are in fact the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for PDE expression should be established. This is accomplished by combining body fluids or cell extracts taken from normal subjects, either animal or human, with PDEXV or a portion thereof, under conditions suitable for hybridisation or amplification. Standard hybridisation may be quantified by comparing the values obtained for normal subjects with a dilution series of positive controls run in the same experiment where a known amount of purified PDEXV is used. Standard values obtained from normal samples may be compared with values obtained from samples from subjects potentially affected by a disorder or disease related to expression of the PDE coding sequence. Deviation between standard and subject values establishes the presence of the disease state. If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

Thus, the present invention relates to the use of a PDEXV polypeptide, or variant, homologue, fragment or derivative thereof, to produce anti-PDEXV antibodies which can, for example, be used diagnostically to detect and quantify PDEXV levels in disease states.

The present invention further provides diagnostic assays and kits for the detection of PDEXV in cells and tissues comprising a purified PDEXV which may be used as a positive control, and anti-PDEXV antibodies. Such antibodies may be used in solution-based, membrane-based, or tissue-based technologies to detect any disease state or condition related to the expression of PDEXV protein or expression of deletions or a variant, homologue, fragment or derivative thereof.

Probes

Another aspect of the subject invention is the provision of nucleic acid hybridisation or PCR probes which are capable of detecting polynucleotide sequences, including genomic sequences, encoding PDE coding region or closely related molecules, such as alleles. The specificity of the probe, i.e., whether it is derived from a highly conserved, conserved or non-conserved region or domain, and the stringency of the hybridisation or amplification (high, intermediate or low) will determine whether the probe identifies only naturally occurring PDE coding sequence, or related sequences.

Probes for the detection of related nucleic acid sequences are selected from conserved or highly conserved nucleotide regions of cyclic nucleotide PDE family members, such as the 3' region, and such probes may be used in a pool of degenerate probes. For the detection of identical nucleic acid sequences, or where maximum specificity is desired, nucleic acid probes are selected from the non-conserved nucleotide regions or unique regions of PDE polynucleotides. As used herein, the term "non-conserved nucleotide region" refers to a nucleotide region that is unique to the PDE coding sequence disclosed herein and does not occur in related family members, such as known cyclic nucleotide PDEs.

PCR as described in U.S. Pat. Nos. 4,683,195, 4,800,195 and 4,965,188 provides additional uses for oligonucleotides based upon the PDEXV sequence. Such oligomers are generally chemically synthesized, but they may be generated enzymatically or produced from a recombinant source. Oligomers generally comprise two nucleotide sequences, one with sense orientation (5'->3') and one with antisense (3'<-5') employed under optimised conditions for identification of a specific gene or condition. The same two oligomers, nested sets of oligomers, or even a degenerate pool of oligomers may be employed under less stringent conditions for detection and/or quantification of closely related DNA or RNA sequences.

The nucleic acid sequence for PDEXV can also be used to generate hybridisation probes as previously described, for mapping the endogenous genomic sequence. The sequence may be mapped to a particular chromosome or to a specific region of the chromosome using well known techniques. These include in situ hybridisation to chromosomal spreads (Verma et al (1988) Human Chromosomes: A Manual of Basic Techniques, Pergamon Press, New York City), flow-sorted chromosomal preparations, or artificial chromosome constructions such as YACs, bacterial artificial chromosomes (BACs), bacterial PI constructions or single chromosome cDNA libraries.

In situ hybridisation of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localised by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. between normal, carrier or affected individuals.

Pharmaceuticals

The present invention also provides a pharmaceutical composition for treating an individual in need of same due to PDEXV activity, the composition comprising a therapeutically effective amount of an agent that affects (such as inhibits) said activity and a pharmaceutically acceptable carrier, diluent, excipient or adjuvant.

Thus, the present invention also covers pharmaceutical compositions comprising the agents of the present invention (an agent capable of modulating the expression pattern of the nucleotide sequence of the present invention or the activity of the expression product thereof and/or an agent identified by an assay according to the present invention). In this regard, and in particular for human therapy, even though the agents of the present invention can be administered alone, they will generally be administered in admixture with a pharmaceutical carrier, excipient or diluent selected with regard to the intended route of administration and standard pharmaceutical practice.

By way of example, in the pharmaceutical compositions of the present invention, the agents of the present invention may be admixed with any suitable binder(s), lubricant(s), suspending agent(s), coating agent(s), or solubilising agent(s).

In general, a therapeutically effective daily oral or intravenous dose of the agents of the present invention is likely to range from 0.01 to 50 mg/kg body weight of the subject to be treated, preferably 0.1 to 20 mg/kg. The agents of the present invention may also be administered by intravenous infusion, at a dose which is likely to range from 0.001–10 mg/kg/hr.

Tablets or capsules of the agents may be administered singly or two or more at a time, as appropriate. It is also possible to administer the agents of the present invention in sustained release formulations.

Thus, the present invention also provides a method of treating an individual in need of same due to PDEXV activity comprising administering to said individual an effective amount of the pharmaceutical composition of the present invention.

Typically, the physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the agents of the present invention may typically be from 10 to 500 mg (in single or divided doses). Thus, and by way of example, tablets or capsules may contain from 5 to 100 mg of active agent for administration singly, or two or more at a time, as appropriate. As indicated above, the physician will determine the actual dosage which will be most suitable for an individual patient and it will vary with the age, weight and response of the particular patient. It is to be noted that whilst the above-mentioned dosages are exemplary of the average case there can, of course, be individual instances where higher or lower dosage ranges are merited and such dose ranges are within the scope of this invention.

In some applications, generally, in humans, oral administration of the agents of the present invention is the preferred route, being the most convenient and can in some cases avoid disadvantages associated with other routes of administration—such as those associated with intracavernosal (i.c.) administration. In circumstances where the recipient suffers from a swallowing disorder or from impairment of drug absorption after oral administration, the drug may be administered parenterally, e.g. sublingually or buccally.

For veterinary use, the agent of the present invention is typically administered as a suitably acceptable formulation in accordance with normal veterinary practice and the veterinary surgeon will determine the dosing regimen and route of administration which will be most appropriate for a particular animal. However, as with human treatment, it may be possible to administer the agent alone for veterinary treatments.

Typically, the pharmaceutical compositions—which may be for human or animal usage—will comprise any one or more of a pharmaceutically acceptable diluent, carrier, excipient or adjuvant. The choice of pharmaceutical carrier, excipient or diluent can be selected with regard to the intended route of administration and standard pharmaceutical practice. As indicated above, the pharmaceutical compositions may comprise as—or in addition to—the carrier, excipient or diluent any suitable binder(s), lubricant(s), suspending agent(s), coating agent(s), solubilising agent(s).

In some embodiments of the present invention, the pharmaceutical compositions will comprise one or more of: an agent that has been screened by an assay of the present invention; an agent that is capable of interacting with any one of the sequences shown in the attached sequence listings including derivatives, fragments, homologues or variants thereof or sequences capable of hybridising to the nucleotide sequence shown in the attached sequence listings.

Included in the scope of the invention are oligonucleotide sequences, antisense RNA and DNA molecules and ribozymes, which function to destabilise PDEXV mRNA or inhibit translation of a PDEXV. Such nucleotide sequences may be used in conditions where it would be preferable to increase cyclic nucleotide levels, such as in inflammation.

A PDEXV antisense molecule may provide the basis for treatment of various abnormal conditions related to, for example, increased PDEXV activity.

A PDEXV nucleic acid antisense molecule may be used to block the activity of the PDEXV in conditions where it would be preferable to elevate cyclic nucleotide levels.

Expression vectors derived from retroviruses, adenovirus, herpes or vaccinia viruses, or from various bacterial plasmids, may be used for delivery of recombinant PDEXV sense or antisense molecules to the targeted cell population. Methods which are well known to those skilled in the art can be used to construct recombinant vectors containing PDEXV. Alternatively, recombinant PDEXV can be delivered to target cells in liposomes.

The full length cDNA sequence and/or its regulatory elements enable researchers to use PDEXV as a tool in sense (Youssoufian H and H F Lodish 1993 Mol Cell Biol 13:98–104) or antisense (Eguchi et al (1991) Annu Rev Biochem 60:631–652) investigations of gene function. Oligonucleotides, designed from the cDNA or control sequences obtained from the genomic DNA can be used in vitro or in vivo to inhibit expression. Such technology is now well known in the art, and sense or antisense oligonucleotides or larger fragments can be designed from various locations along the coding or control regions. Appropriate oligonucleotides, which can be 20 nucleotides in length, may be used to isolate PDEXV sequences or closely related molecules from human libraries.

Additionally, PDEXV expression can be modulated by transfecting a cell or tissue with expression vectors which express high levels of a PDEXV fragment in conditions where it would be preferable to block phosphodiesterase activity thereby increasing cyclic nucleotide levels. Such constructs can flood cells with untranslatable sense or antisense sequences. Even in the absence of integration into the DNA, such vectors may continue to transcribe RNA molecules until all copies of the vector are disabled by endogenous nucleases. Such transient expression may last for a month or more with a non-replicating vector and even longer if appropriate replication elements are part of the vector system.

Modifications of gene expression can be obtained by designing antisense sequences to the control regions of the PDE gene, such as the promoters, enhancers, and introns.

Oligonucleotides derived from the transcription initiation site, e.g., between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom base-pairing methodology, also known as "triple helix" base pairing. Triple helix pairing compromises the ability of the double helix to open sufficiently for the binding of polymerases, transcription factors, or regulatory molecules.

Thus the invention provides a pharmaceutical composition comprising an agent of the present invention (or even a pharmaceutically acceptable salt thereof, or a pharmaceutically acceptable solvate thereof) together with a pharmaceutically acceptable diluent, excipient or carrier.

The pharmaceutical composition could be for veterinary (i.e. animal) usage or for human usage.

Thus, the present invention therefore also relates to pharmaceutical compositions comprising effective amounts of inhibitors or antagonists of PDEXV protein (including antisense nucleic acid sequences) in admixture with a pharmaceutically acceptable diluent, carrier, excipient or adjuvant (including combinations thereof).

The present invention relates to pharmaceutical compositions which may comprise all or portions of PDEXV polynucleotide sequences, PDEXV antisense molecules, PDEXV polypeptides, protein, peptide or organic modulators of PDEXV bioactivity, such as inhibitors, antagonists (including antibodies) or agonists, alone or in combination with at least one other agent, such as stabilising compound, and may be administered in any sterile, biocompatible pharmaceutical carrier, including, but not limited to, saline, buffered saline, dextrose, and water.

General Methodology References

Although in general the techniques mentioned herein are well known in the art, reference may be made in particular to Sambrook et al., Molecular Cloning, A Laboratory Manual (1989) and Ausubel et al., Short Protocols in Molecular Biology (1999) 4$^{th}$ Ed, John Wiley & Sons, Inc. PCR is described in U.S. Pat. Nos. 4,683,195, 4,800,195 and 4,965,188.

Deposits

The following sample was deposited in accordance with the Budapest Treaty at the recognised depositary The National Collections of Industrial and Marine Bacteria Limited (NCIMB) at 23 St. Machar Drive, Aberdeen, Scotland, United Kingdom, AB2 1RY on 9 Sep. 1999:

NCIMB number NCIMB 41025 is *Escherichia coli* (pH-SPDExv).

The depositor was Pfizer Central Research, Pfizer Limited, Ramsgate Road, Sandwich, Kent, CT13 9NJ, United Kingdom.

The present invention also encompasses sequences derivable and/or expressable from that deposit and embodiments comprising the same. The present invention also encompasses partial sequences derivable and/or expressable from that deposit and embodiments comprising the same, wherein those partial sequences code for active enzymatic sites. The present invention also encompasses proteins comprising sequences derivable and/or expressable from that deposit and embodiments comprising the same. The present invention also encompasses proteins comprising partial sequences derivable and/or expressable from that deposit and embodiments comprising the same, wherein those partial sequences code for active enzymatic sites.

The present invention also encompasses sequences derivable and/or expressable from that deposit and embodiments comprising the same.

The present invention will now be described, by way of example only.

EXAMPLES

PDEXV cDNA Isolation

Materials and Methods

5' RACE: Reaction buffers and enzymes were obtained in kit format from Life technologies. Protocol was carried out according to the Instruction manual ([Life technologies] 5'RACE system for rapid amplification of cDNA ends, version 2. Cat No. 18374-058), using the modification of dA tailing the first strand cDNA.

```
Anchor primer:   5'-GGCCACGCGTCGACTAGTACTTTTTTTTTTTTTTTTT-3'   (SEQ ID NO:9)

Adapter primer:  5'-GGCCACGCGTCGACTAGTAC-3'                    (SEQ ID NO:10)
```

Expression: PDExv was expressed using the baculovirus system as detailed later.

Results

Original sequence identified in the IMAGE EST database by keyword searching (IMAGE clone #1639772—isolated from human testis library)

In order to obtain the complete 5' sequence of the splice variant, 5' rapid amplification of cDNA ends (RACE) was carried out on testis poly A$^+$RNA (Clontech)

```
GSP1:  5'-CAGAACAGCGTTCACATTTCAGC-3'   (SEQ ID NO:11)

GSP2:  5'-AGGTCAGTCTGTTCTTCAAAGAGG-3'  (SEQ ID NO:12)

GSP3:  5'-CAGTAAATGGAGCTCCTTCAGG-3'    (SEQ ID NO:13)
``` cDNA was generated from the testis poly A$^+$RNA using GSP1 as the synthesis primer.

First round PCR on this cDNA was carried out using GSP2 as the 3' primer and the anchor primer supplied with the kit. Nested PCR on the first round products were carried out using GSP3 as the 3' primer and the 5' adapter primer supplied with the kit. The nested RACE products were used to generate a mini-library of 1500 clones in the TOPO-TA cloning vector (PCR2.1-TOPO, Invitrogen). This mini-library was screened by hybridisation with an oligonucleotide probe GSP4.

GSP4: 5'-TTGTGCATGCCTATCCGAAGCAGTTATGGT-3' (SEQ ID NO:14)

8 clones were identified on sequencing proved to extend the known PDE11 sequence. Using this extended sequence, a 5' primer (GSP5) was designed to allow cloning of the new sequence into the expression vector pFASTBAC-FLAG. This primer contains an engineered RsrII site.

```
GSP5:  5'-GCACGGTCCGAGATGCTGAAGCAGG-3'  (SEQ ID NO:15)

GSP6:  5'-AGATATCTGGTCTGCCTCTGC-3'     (SEQ ID NO:16)
```

PCR using GSP5 (5' primer) and GSP6 (3' primer) generated a 780 bp fragment containing a 5' engineered RsrII site and a natural StuI site.

The original PDE11A1 (PDE10-Incyte) expression construct in pFASTBAC, and the above 780 bp fragment, were digested with restriction endonucleases RsrII and StuI. The 780 bp fragment was ligated to the 3' end of PDE11A1 to generate the extended splice variant PDExv (PDE11A3). The entire PDExv construct was then cloned into pFAST-BAC-FLAG.

Expression: The recombinant enzyme hydrolyses both cGMP and cAMP.

Baculovirus Expression

The following studies demonstrate that the PDE enzyme of the present invention—called PDE here for short—can be generated using a baculovirus expression system.

The following studies also demonstrate that the PDE shows cyclic nucleotide hydrolytic activity when it has been expressed in the baculovirus system.

The PDE enzyme was generated using the baculovirus expression system based on *Autographa californica* nuclear polyhedrosis virus (AcNPV) infection of *Spodoptera frugiperda* insect cells (Sf9 cells).

In these studies, cDNA encoding PDE was cloned into the donor plasmid pFASTBAC-FLAG which contains a mini-Tn7 transposition element. The recombinant plasmid was transformed into DH10BAC competent cells which contain the parent bacmid bMON14272 (AcNPV infectious DNA) and a helper plasmid. The mini-Tn7 element on the pFAST-BAC donor can transpose to the attTn7 attachment site on the bacmid thus introducing the PDE gene into the viral genome. Colonies containing recombinant bacmids are identified by disruption of the lacZ gene. The PDE/bacmid construct can then be isolated and infected into insect cells (Sf9 cells) resulting in the production of infectious recombinant baculovirus particles and expression of recombinant PDE-FLAG fusion protein.

The phosphodiesterase activity of the crude cell extracts was measured.

Cells were harvested and extracts prepared 24, 48 and 72 hours after transfection.

These results confirm that PDE cDNA encodes a phosphodiesterase which is able to hydrolyse cAMP and/or cGMP.

The crude lysate material was purified by FPLC using a column containing agarose beads (M2 affinity gel) to which a purified IgG₁ monoclonal anti-FLAG antibody had been conjugated by hydrazide linkage (Eastman Kodak). This allows the specific retention on the column of the recombinant material (since this is fused to the FLAG epitope) whilst the endogenous insect proteins are washed off in the eluate. The recombinant material is then washed off under conditions of low pH. This purified material was more suitable for detailed enzymatic and inhibitor studies. The purity of the material is assessed by coomassie staining after sodium dodecyl sulphate-polyacrylamide gel electrophoresis (SDS-PAGE) or through western blotting onto a nitro-cellulose membrane of an unstained SDS-PAGE (containing recombinant PDE) and analysis with the IgG1 monoclonal anti-FLAG epitope antibody. The PDE-FLAG fusion protein is detected due to the interaction between the anti-FLAG antibody and the FLAG epitope which is fused to the PDE protein.

The phosphodiesterase activity of the purified PDE-FLAG fusion protein was assayed using a commercially available SPA (scintillation proximity assay) kit (Amersham—Amersham place, Little Chalfont, Bucks, HP7 9NA UK) for either cAMP and/or cGMP hydrolytic activity. This can be used to permit the determination of the Km value for PDE against cAMP and/or cGMP by determining the enzyme activity at a range of substrate concentrations allowing the calculation of an approximate Vmax value for the enzyme.

The results of these experiments show that the PDE cDNA encodes a phosphodiesterase which is able to hydrolyse cAMP and/or cGMP.

SUMMARY

In summary the present invention provides:
1. Novel amino acids.
2. Novel nucleotide sequences.
3. Assays using said novel sequences.
4. Compounds/compositions identified by use of said assays.
5. Expression systems comprising or expressing said novel sequences.
6. Methods of treatment based on said novel sequences.
7. Pharmaceutical compositions based on said novel sequences.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

Sequences

These are the amino acid and nucleotide sequences of PDEXV.

```
SEQ ID NO: 1

MLKQARRPLFRNVLSATQWKKVKITRLVQISGASLAEKQEKHQDFLIQRQTKTKDRRFND

EIDKLTGYKTKSLLCMPIRSSDGEIIGVAQAINKIPEGAPFTEDDEKVMQMYLPFCGIAISN

AQLFAASRKEYERSRALLEVVNDLFEEQTDLEKIVKKIMHRAQTLLKCERCSVLLLEDIES

PVVKFTKSFELMSPKCSADAENSFKESMEKSSYSDWLINNSIAELVASTGLPVNISDAYQ

DPRFDAEADQISGFHIRSVLCVPIWNSNHQIIGVAQVLNRLDGKPFDDADQRLFEAFVIFC

GLGINNTIMYDQVKKSWAKQSVALDVLSYHATCSKAEVDKFKAANIPLVSELAIDDIHFDD

FSLDVDAMITAALRMFMELGMVQKFKIDYETLCRWLLTVRKNYRMVLYHNWRHAFNVC

QLMFAMLTTAGFQDILTEVEILAVIVGCLCHDLDHRGTNNAFQAKSGSALAQLYGTSATL

EHHHFNHAVMILQSEGHNIFANLSSKEYSDLMQLLKQSILATDLTLYFERRTEFFELVSKG

EYDWNIKNHRDIFRSMLMTACDLGAVTKPWEISRQVAELVTSEFFEQGDRERLELKLTPS

AIFDRNRKDELPRLQLEWIDSICMPLYQALVKVNVKLKPMLDSVATNRSKWEELHQKRLL
```

ASTASSSSPASVMVAKEDRN

SEQ ID NO: 2

GGTCCGAGATGCTGAAGCAGGCAAGAAGACCTTTATTCAGAAATGTGCTCAGTGCC

ACACAGTGGAAAAAGGTGAAAATCACAAGACTGGTCCAAATCTCTGGGGCCTCTTTG

GCTGAAAAACAGGAAAAGCACCAGGATTTTCTTATACAGAGGCAAACAAAAACAAAG

GATCGACGATTCAATGATGAAATCGACAAGCTGACTGGATACAAGACAAAATCATTAT

TGTGCATGCCTATCCGAAGCAGTGATGGTGAGATTATTGGTGTGGCCCAAGCGATA

AATAAGATTCCTGAAGGAGCTCCATTTACTGAAGATGATGAAAAAGTTATGCAGATGT

ATCTTCCATTTTGTGGAATCGCCATATCTAACGCTCAGCTCTTTGCTGCCTCAAGGAA

AGAATATGAAAGAAGCAGAGCTTTGCTAGAGGTGGTTAATGACCTCTTTGAAGAACA

GACTGACCTGGAGAAAATTGTCAAGAAAATAATGCATCGGGCCCAAACTCTGCTGAA

ATGTGAGCGCTGTTCTGTTTTACTCCTAGAGGACATCGAATCACCAGTGGTGAAATT

TACCAAATCCTTTGAATTGATGTCCCCAAAGTGCAGTGCTGATGCTGAGAACAGTTT

CAAAGAAAGCATGGAGAAATCATCATACTCCGACTGGCTAATAAATAACAGCATTGCT

GAGCTGGTTGCTTCAACAGGCCTTCCAGTGAACATCAGTGATGCCTACCAGGATCC

GCGCTTTGATGCAGAGGCAGACCAGATATCTGGTTTTCACATAAGATCTGTTCTTTG

TGTCCCTATTTGGAATAGCAACCACCAAATAATTGGAGTGGCTCAAGTGTTAAACAG

ACTTGATGGGAAACCTTTTGATGATGCAGATCAACGACTTTTTGAGGCTTTTGTCATC

TTTTGTGGACTTGGCATCAACAACACAATTATGTATGATCAAGTGAAGAAGTCCTGG

GCCAAGCAGTCTGTGGCTCTTGATGTGCTATCATACCATGCAACATGTTCAAAAGCT

GAAGTTGACAAGTTTAAGGCAGCCAACATCCCTCTGGTGTCAGAACTTGCCATCGAT

GACATTCATTTTGATGACTTTTCTCTCGACGTTGATGCCATGATCACAGCTGCTCTCC

GGATGTTCATGGAGCTGGGGATGGTACAGAAATTTAAAATTGACTATGAGACACTGT

GTAGGTGGCTTTTGACAGTGAGGAAAAACTATCGGATGGTTCTATACCACAACTGGA

GACATGCCTTCAACGTGTGTCAGCTGATGTTCGCGATGTTAACCACTGCTGGGTTTC

AAGACATTCTGACCGAGGTGGAAATTTTAGCGGTGATTGTGGGATGCCTGTGTCATG

ACCTCGACCACAGGGGAACCAACAATGCCTTCCAAGCTAAGAGTGGCTCTGCCCTG

GCCCAACTCTATGGAACCTCTGCTACCTTGGAGCATCACCATTTCAACCACGCCGTG

ATGATCCTTCAAAGTGAGGGTCACAATATCTTTGCTAACCTGTCCTCCAAGGAATATA

GTGACCTTATGCAGCTTTTGAAGCAGTCAATATTGGCAACAGACCTCACGCTGTACT

TTGAGAGGAGAACTGAATTCTTTGAACTTGTCAGTAAAGGAGAATACGATTGGAACA

TCAAAAACCATCGTGATATATTTCGATCAATGTTAATGACAGCCTGTGACCTTGGAGC

CGTGACCAAACCGTGGGAGATCTCCAGACAGGTGGCAGAACTTGTAACCAGTGAGT

TCTTCGAACAAGGAGATCGGGAGAGATTAGAGCTCAAACTCACTCCTTCAGCAATTT

TTGATCGGAACCGGAAGGATGAACTGCCTCGGTTGCAACTGGAGTGGATTGATAGC

ATCTGCATGCCTTTGTATCAGGCACTGGTGAAGGTCAACGTGAAACTGAAGCCGATG

CTAGATTCAGTAGCTACAAACAGAAGTAAGTGGGAAGAGCTACACCAAAAACGACTG

CTGGCCTCAACTGCCTCATCCTCCTCCCCTGCCAGTGTTATGGTAGCCAAGGAAGAC

AGGAACTAATAACTCGAGGCATGC

The invention claimed is:

1. An isolated polypeptide selected from the group consisting of:
   (a) a polypeptide comprising the amino acid sequence as set forth in SEQ ID NO: 1, and
   (b) a polypeptide comprising an amino acid sequence having at least 95% identity to the amino acid sequence set forth in SEQ ID NO: 1, wherein the said isolated polypeptide has phosphodiesterase activity.

2. The isolated polypeptide of claim 1, consisting of the amino acid sequence as set forth in SEQ ID NO: 1.

3. The isolated polypeptide of claim 1, comprising the amino acid sequence of amino acids 1–194 as set forth in SEQ ID NO: 1.

4. An isolated polypeptide of claim 1, comprising the amino acid sequence as set forth in SEQ ID NO: 7.

5. The isolated polypeptide of claim 1, comprising at least 25 contiguous amino acids selected from the amino acids 1–194 as set forth in SEQ ID NO:1.

6. A method of producing the polypeptide of claim 1, the method comprising:
   (a) culturing a cell under conditions suitable for the expression of the polypeptide, wherein said cell is transformed with a recombinant polynucleotide, and said recombinant polynucleotide comprises a promoter sequence operatively linked to a polynucleotide encoding the polypeptide of claim 1, and
   (b) recovering the polypeptide so expressed.

7. The method of claim 6, wherein the isolated polypeptide has the amino acid sequence as set forth in SEQ ID NO: 1.

8. The method of claim 6, wherein the isolated polypeptide is expressful from a nucleic acid sequence obtainable from NCIMB-41025.

9. The method of claim 6, wherein the recombinant polynucleotide comprises the nucleic acid sequence as set forth in SEQ ID NO: 2.

10. An isolated polypeptide selected from the group consisting of:
    (a) an amino acid sequence as set forth in SEQ ID NO. 7, and
    (b) an isolated polypeptide having 95% identity to the amino acid sequence as set forth in SEQ ID NO: 7.

11. An isolated polypeptide of claim 10 comprising 25 contiguous amino acids selected from the amino acids as set forth in SEQ ID NO: 7.

12. An isolated or purified polypeptide comprising the amino acid sequence as set forth in SEQ ID NO:1 or amino acids 1–194 of SEQ ID NO:1.

13. An isolated or purified polypeptide comprising 25 contiguous amino acids of SEQ ID NO:7.

* * * * *

SEQUENCE LISTING

<160> NUMBER OF SEQ ID NOS: 16

<210> SEQ ID NO 1
<211> LENGTH: 684
<212> TYPE: PRT
<213> ORGANISM: Homo sapiens

<400> SEQUENCE: 1

```
Met Leu Lys Gln Ala Arg Arg Pro Leu Phe Arg Asn Val Leu Ser Ala
1               5                   10                  15

Thr Gln Trp Lys Lys Val Lys Ile Thr Arg Leu Val Gln Ile Ser Gly
            20                  25                  30

Ala Ser Leu Ala Glu Lys Gln Glu Lys His Gln Asp Phe Leu Ile Gln
        35                  40                  45

Arg Gln Thr Lys Thr Lys Asp Arg Arg Phe Asn Asp Glu Ile Asp Lys
    50                  55                  60

Leu Thr Gly Tyr Lys Thr Lys Ser Leu Leu Cys Met Pro Ile Arg Ser
65                  70                  75                  80

Ser Asp Gly Glu Ile Ile Gly Val Ala Gln Ala Ile Asn Lys Ile Pro
                85                  90                  95

Glu Gly Ala Pro Phe Thr Glu Asp Glu Lys Val Met Gln Met Tyr
            100                 105                 110

Leu Pro Phe Cys Gly Ile Ala Ile Ser Asn Ala Gln Leu Phe Ala Ala
        115                 120                 125

Ser Arg Lys Glu Tyr Glu Arg Ser Arg Ala Leu Leu Glu Val Val Asn
    130                 135                 140

Asp Leu Phe Glu Glu Gln Thr Asp Leu Glu Lys Ile Val Lys Lys Ile
145                 150                 155                 160

Met His Arg Ala Gln Thr Leu Leu Lys Cys Glu Arg Cys Ser Val Leu
                165                 170                 175

Leu Leu Glu Asp Ile Glu Ser Pro Val Val Lys Phe Thr Lys Ser Phe
            180                 185                 190

Glu Leu Met Ser Pro Lys Cys Ser Ala Asp Ala Glu Asn Ser Phe Lys
        195                 200                 205

Glu Ser Met Glu Lys Ser Ser Tyr Ser Asp Trp Leu Ile Asn Asn Ser
    210                 215                 220

Ile Ala Glu Leu Val Ala Ser Thr Gly Leu Pro Val Asn Ile Ser Asp
225                 230                 235                 240

Ala Tyr Gln Asp Pro Arg Phe Asp Ala Glu Ala Asp Gln Ile Ser Gly
                245                 250                 255

Phe His Ile Arg Ser Val Leu Cys Val Pro Ile Trp Asn Ser Asn His
            260                 265                 270

Gln Ile Ile Gly Val Ala Gln Val Leu Asn Arg Leu Asp Gly Lys Pro
        275                 280                 285

Phe Asp Asp Ala Asp Gln Arg Leu Phe Glu Ala Phe Val Ile Phe Cys
    290                 295                 300

Gly Leu Gly Ile Asn Asn Thr Ile Met Tyr Asp Gln Val Lys Lys Ser
305                 310                 315                 320

Trp Ala Lys Gln Ser Val Ala Leu Asp Val Leu Ser Tyr His Ala Thr
                325                 330                 335

Cys Ser Lys Ala Glu Val Asp Lys Phe Lys Ala Ala Asn Ile Pro Leu
            340                 345                 350

Val Ser Glu Leu Ala Ile Asp Asp Ile His Phe Asp Asp Phe Ser Leu
```

Asp Val Asp Ala Met Ile Thr Ala Ala Leu Arg Met Phe Met Glu Leu
370                 375                 380

Gly Met Val Gln Lys Phe Lys Ile Asp Tyr Glu Thr Leu Cys Arg Trp
385                 390                 395                 400

Leu Leu Thr Val Arg Lys Asn Tyr Arg Met Val Leu Tyr His Asn Trp
            405                 410                 415

Arg His Ala Phe Asn Val Cys Gln Leu Met Phe Ala Met Leu Thr Thr
                420                 425                 430

Ala Gly Phe Gln Asp Ile Leu Thr Glu Val Glu Ile Leu Ala Val Ile
            435                 440                 445

Val Gly Cys Leu Cys His Asp Leu Asp His Arg Gly Thr Asn Asn Ala
450                 455                 460

Phe Gln Ala Lys Ser Gly Ser Ala Leu Ala Gln Leu Tyr Gly Thr Ser
465                 470                 475                 480

Ala Thr Leu Glu His His His Phe Asn His Ala Val Met Ile Leu Gln
                485                 490                 495

Ser Glu Gly His Asn Ile Phe Ala Asn Leu Ser Ser Lys Glu Tyr Ser
            500                 505                 510

Asp Leu Met Gln Leu Leu Lys Gln Ser Ile Leu Ala Thr Asp Leu Thr
            515                 520                 525

Leu Tyr Phe Glu Arg Arg Thr Glu Phe Phe Glu Leu Val Ser Lys Gly
            530                 535                 540

Glu Tyr Asp Trp Asn Ile Lys Asn His Arg Asp Ile Phe Arg Ser Met
545                 550                 555                 560

Leu Met Thr Ala Cys Asp Leu Gly Ala Val Thr Lys Pro Trp Glu Ile
                565                 570                 575

Ser Arg Gln Val Ala Glu Leu Val Thr Ser Glu Phe Phe Glu Gln Gly
            580                 585                 590

Asp Arg Glu Arg Leu Glu Leu Lys Leu Thr Pro Ser Ala Ile Phe Asp
            595                 600                 605

Arg Asn Arg Lys Asp Glu Leu Pro Arg Leu Gln Leu Glu Trp Ile Asp
610                 615                 620

Ser Ile Cys Met Pro Leu Tyr Gln Ala Leu Val Lys Val Asn Val Lys
625                 630                 635                 640

Leu Lys Pro Met Leu Asp Ser Val Ala Thr Asn Arg Ser Lys Trp Glu
                645                 650                 655

Glu Leu His Gln Lys Arg Leu Leu Ala Ser Thr Ala Ser Ser Ser Ser
            660                 665                 670

Pro Ala Ser Val Met Val Ala Lys Glu Asp Arg Asn
            675                 680

<210> SEQ ID NO 2
<211> LENGTH: 2078
<212> TYPE: DNA
<213> ORGANISM: Homo sapiens

<400> SEQUENCE: 2

```
ggtccgagat gctgaagcag gcaagaagac ctttattcag aaatgtgctc agtgccacac      60
agtggaaaaa ggtgaaaatc acaagactgg tccaaatctc tggggcctct ttggctgaaa     120
aacaggaaaa gcaccaggat tttcttatac agaggcaaac aaaaacaaag gatcgacgat     180
tcaatgatga aatcgacaag ctgactggat acagacaaa atcattattg tgcatgccta     240
tccgaagcag tgatggtgag attattggtg tggcccaagc gataaataag attcctgaag     300
```

```
gagctccatt tactgaagat gatgaaaaag ttatgcagat gtatcttcca ttttgtggaa      360
tcgccatatc taacgctcag ctctttgctg cctcaaggaa agaatatgaa agaagcagag      420
ctttgctaga ggtggttaat gacctctttg aagaacagac tgacctggag aaaattgtca      480
agaaaataat gcatcgggcc caaactctgc tgaaatgtga gcgctgttct gttttactcc      540
tagaggacat cgaatcacca gtggtgaaat ttaccaaatc ctttgaattg atgtccccaa      600
agtgcagtgc tgatgctgag aacagtttca agaaagcat ggagaaatca tcatactccg       660
actggctaat aaataacagc attgctgagc tggttgcttc aacaggcctt ccagtgaaca      720
tcagtgatgc ctaccaggat ccgcgctttg atgcagaggc agaccagata tctggttttc      780
acataagatc tgttctttgt gtccctattt ggaatagcaa ccaccaaata attggagtgg      840
ctcaagtgtt aaacagactt gatgggaaac cttttgatga tgcagatcaa cgacttttttg     900 aggcttttgt catcttttgt ggacttggca tcaacaacac aattatgtat gatcaagtga      960
agaagtcctg ggccaagcag tctgtggctc ttgatgtgct atcataccat gcaacatgtt     1020
caaaagctga agttgacaag tttaaggcag ccaacatccc tctggtgtca gaacttgcca     1080
tcgatgacat tcattttgat gacttttctc tcgacgttga tgccatgatc acagctgctc     1140
tccggatgtt catggagctg gggatggtac agaaatttaa aattgactat gagacactgt     1200
gtaggtggct tttgacagtg aggaaaaact atcggatggt tctataccac aactggagac     1260
atgccttcaa cgtgtgtcag ctgatgttcg cgatgttaac cactgctggg tttcaagaca     1320
ttctgaccga ggtggaaatt ttagcggtga ttgtgggatg cctgtgtcat gacctcgacc     1380 acagggggaac caacaatgcc ttccaagcta agagtggctc tgccctggcc caactctatg     1440
gaacctctgc taccttggag catcaccatt tcaaccacgc cgtgatgatc cttcaaagtg     1500
agggtcacaa tatctttgct aacctgtcct ccaaggaata tagtgacctt atgcagcttt     1560
tgaagcagtc aatattggca acagacctca cgctgtactt tgagaggaga actgaattct     1620
ttgaacttgt cagtaaagga gaatacgatt ggaacatcaa aaaccatcgt gatatatttc     1680
gatcaatgtt aatgacagcc tgtgaccttg agccgtgac caaaccgtgg gagatctcca     1740
gacaggtggc agaacttgta accagtgagt tcttcgaaca aggagatcgg gagagattag     1800
agctcaaact cactccttca gcaattttttg atcggaaccg gaaggatgaa ctgcctcggt     1860
tgcaactgga gtggattgat agcatctgca tgcctttgta tcaggcactg gtgaaggtca     1920
acgtgaaact gaagccgatg ctagattcag tagctacaaa cagaagtaag tgggaagagc     1980
tacaccaaaa acgactgctg gcctcaactg cctcatcctc ctcccctgcc agtgttatgg     2040
tagccaagga agacaggaac taataactcg aggcatgc                             2078
```

<210> SEQ ID NO 3
<211> LENGTH: 576
<212> TYPE: PRT
<213> ORGANISM: Homo sapiens

<400> SEQUENCE: 3

Met Gln Met Tyr Leu Pro Phe Cys Gly Ile Ala Ile Ser Asn Ala Gln
1               5                   10                  15

Leu Phe Ala Ala Ser Arg Lys Glu Tyr Glu Arg Ser Arg Ala Leu Leu
            20                  25                  30

Glu Val Val Asn Asp Leu Phe Glu Glu Gln Thr Asp Leu Glu Lys Ile
        35                  40                  45

Val Lys Lys Ile Met His Arg Ala Gln Thr Leu Leu Lys Cys Glu Arg

-continued

```
                50                  55                  60
Cys Ser Val Leu Leu Glu Asp Ile Glu Ser Pro Val Val Lys Phe
65                  70                  75                  80

Thr Lys Ser Phe Glu Leu Met Ser Pro Lys Cys Ser Ala Asp Ala Glu
                85                  90                  95

Asn Ser Phe Lys Glu Ser Met Glu Lys Ser Ser Tyr Ser Asp Trp Leu
                100                 105                 110

Ile Asn Asn Ser Ile Ala Glu Leu Val Ala Ser Thr Gly Leu Pro Val
                115                 120                 125

Asn Ile Ser Asp Ala Tyr Gln Asp Pro Arg Phe Asp Ala Glu Ala Asp
130                 135                 140

Gln Ile Ser Gly Phe His Ile Arg Ser Val Leu Cys Val Pro Ile Trp
145                 150                 155                 160

Asn Ser Asn His Gln Ile Ile Gly Val Ala Gln Val Leu Asn Arg Leu
                165                 170                 175

Asp Gly Lys Pro Phe Asp Asp Ala Asp Gln Arg Leu Phe Glu Ala Phe
                180                 185                 190

Val Ile Phe Cys Gly Leu Gly Ile Asn Asn Thr Ile Met Tyr Asp Gln
                195                 200                 205

Val Lys Lys Ser Trp Ala Lys Gln Ser Val Ala Leu Asp Val Leu Ser
210                 215                 220

Tyr His Ala Thr Cys Ser Lys Ala Glu Val Asp Lys Phe Lys Ala Ala
225                 230                 235                 240

Asn Ile Pro Leu Val Ser Glu Leu Ala Ile Asp Asp Ile His Phe Asp
                245                 250                 255

Asp Phe Ser Leu Asp Val Asp Ala Met Ile Thr Ala Ala Leu Arg Met
                260                 265                 270

Phe Met Glu Leu Gly Met Val Gln Lys Phe Lys Ile Asp Tyr Glu Thr
                275                 280                 285

Leu Cys Arg Trp Leu Leu Thr Val Arg Lys Asn Tyr Arg Met Val Leu
                290                 295                 300

Tyr His Asn Trp Arg His Ala Phe Asn Val Cys Gln Leu Met Phe Ala
305                 310                 315                 320

Met Leu Thr Thr Ala Gly Phe Gln Asp Ile Leu Thr Glu Val Glu Ile
                325                 330                 335

Leu Ala Val Ile Val Gly Cys Leu Cys His Asp Leu Asp His Arg Gly
                340                 345                 350

Thr Asn Asn Ala Phe Gln Ala Lys Ser Gly Ser Ala Leu Ala Gln Leu
                355                 360                 365

Tyr Gly Thr Ser Ala Thr Leu Glu His His Phe Asn His Ala Val
                370                 375                 380

Met Ile Leu Gln Ser Glu Gly His Asn Ile Phe Ala Asn Leu Ser Ser
385                 390                 395                 400

Lys Glu Tyr Ser Asp Leu Met Gln Leu Leu Lys Gln Ser Ile Leu Ala
                405                 410                 415

Thr Asp Leu Thr Leu Tyr Phe Glu Arg Arg Thr Glu Phe Phe Glu Leu
                420                 425                 430

Val Ser Lys Gly Glu Tyr Asp Trp Asn Ile Lys Asn His Arg Asp Ile
                435                 440                 445

Phe Arg Ser Met Leu Met Thr Ala Cys Asp Leu Gly Ala Val Thr Lys
                450                 455                 460

Pro Trp Glu Ile Ser Arg Gln Val Ala Glu Leu Val Thr Ser Glu Phe
465                 470                 475                 480
```

```
Phe Glu Gln Gly Asp Arg Glu Arg Leu Glu Leu Lys Leu Thr Pro Ser
                485                 490                 495
Ala Ile Phe Asp Arg Asn Arg Lys Asp Glu Leu Pro Arg Leu Gln Leu
                500                 505                 510
Glu Trp Ile Asp Ser Ile Cys Met Pro Leu Tyr Gln Ala Leu Val Lys
            515                 520                 525
Val Asn Val Lys Leu Lys Pro Met Leu Asp Ser Val Ala Thr Asn Arg
        530                 535                 540
Ser Lys Trp Glu Glu Leu His Gln Lys Arg Leu Leu Ala Ser Thr Ala
545                 550                 555                 560
Ser Ser Ser Ser Pro Ala Ser Val Met Val Ala Lys Glu Asp Arg Asn
                565                 570                 575
```

<210> SEQ ID NO 4
<211> LENGTH: 1925
<212> TYPE: DNA
<213> ORGANISM: Homo sapiens

<400> SEQUENCE: 4

| | | | | | |
|---|---|---|---|---|---|
| gcaataggaa | gccatggaac | agccagaaag | gttatgcaga | tgtatcttcc | attttgtgga | 60 |
| atcgccatat | ctaacgctca | gctctttgct | gcctcaagga | agaatatga | aagaagcaga | 120 |
| gctttgctag | aggtggttaa | tgacctcttt | gaagaacaga | ctgacctgga | gaaaattgtc | 180 |
| aagaaaataa | tgcatcgggc | ccaaactctg | ctgaaatgtg | aacgctgttc | tgttttactc | 240 |
| ctagaggaca | tcgaatcacc | agtggtgaaa | tttaccaaat | cctttgaatt | gatgtcccca | 300 |
| aagtgcagtg | ctgatgctga | gaacagtttc | aaagaaagca | tggagaaatc | atcatactcc | 360 |
| gactggctaa | taaataacag | cattgctgag | ctggttgctt | caacaggcct | tccagtgaac | 420 |
| atcagtgatg | cctaccagga | tccgcgcttt | gatgcagagg | cagaccagat | atctggtttt | 480 |
| cacataagat | ctgttctttg | tgtccctatt | tggaatagca | accaccaaat | aattggagtg | 540 |
| gctcaagtgt | taaacagact | tgatgggaaa | ccttttgatg | atgcggatca | acgactttt | 600 |
| gaggcttttg | tcatcttttg | tggacttggc | atcaacaaca | caattatgta | tgatcaagtg | 660 |
| aagaagtcct | gggccaagca | gtctgtggct | cttgatgtgc | tatcatacca | tgcaacatgt | 720 |
| tcaaaagctg | aagttgacaa | gtttaaggca | gccaacatcc | ctctggtgtc | agaacttgcc | 780 |
| atcgatgaca | ttcattttga | tgacttttct | ctcgacgttg | atgccatgat | cacagctgct | 840 |
| ctccggatgt | tcatggagct | ggggatggta | cagaaattta | aaattgacta | tgagacactg | 900 |
| tgtaggtggc | ttttgacagt | gaggaaaaac | tatcggatgg | ttctatacca | caactggaga | 960 |
| catgccttca | acgtgtgtca | gctgatgttc | gcgatgttaa | ccactgctgg | gtttcaagac | 1020 |
| attctgaccg | aggtggaaat | tttagcggtg | attgtgggat | gcctgtgtca | tgacctcgac | 1080 |
| cacagggaa | ccaacaatgc | cttccaagct | aagagtggct | ctgccctggc | ccaactctat | 1140 |
| ggaacctctg | ctaccttgga | gcatcaccat | ttcaaccacg | ccgtgatgat | ccttcaaagt | 1200 |
| gagggtcaca | atatctttgc | taacctgtcc | tccaaggaat | atagtgacct | tatgcagctt | 1260 |
| ttgaagcagt | caatattggc | aacagacctc | acgctgtact | tgagaggag | aactgaattc | 1320 |
| tttgaacttg | tcagtaaagg | agaatacgat | tggaacatca | aaaccatcg | tgatatattt | 1380 |
| cgatcaatgt | taatgacagc | ctgtgacctt | ggagccgtga | ccaaaccgtg | ggagatctcc | 1440 |
| agacaggtgg | cagaacttgt | aaccagtgag | ttcttcgaac | aaggagatcg | ggagagatta | 1500 |
| gagctcaaac | tcactccttc | agcaattttt | gatcggaacc | ggaaggatga | actgcctcgg | 1560 |

-continued

```
ttgcaactgg agtggattga tagcatctgc atgcctttgt atcaggcact ggtgaaggtc    1620
aacgtgaaac tgaagccgat gctagattca gtagctacaa acagaagtaa gtgggaagag    1680
ctacaccaaa aacgactgct ggcctcaact gcctcatcct cctcccctgc cagtgttatg    1740
gtagccaagg aagacaggaa ctaaacctcc aggtcagctg cagctgcaaa atgactacag    1800
cctgaagggc cattttcagt ccagcaatgt catccttttg ttcttttagc tcagaaagac    1860
ctaacatctc aaggatgcac tgggaaccat gcctgggctt tcaccttgaa gcatggtcag    1920
cagca                                                                1925
```

<210> SEQ ID NO 5
<211> LENGTH: 490
<212> TYPE: PRT
<213> ORGANISM: Homo sapiens

<400> SEQUENCE: 5

```
Met Ser Pro Lys Cys Ser Ala Asp Ala Glu Asn Ser Phe Lys Glu Ser
1               5                   10                  15

Met Glu Lys Ser Ser Tyr Ser Asp Trp Leu Ile Asn Asn Ser Ile Ala
            20                  25                  30

Glu Leu Val Ala Ser Thr Gly Leu Pro Val Asn Ile Ser Asp Ala Tyr
        35                  40                  45

Gln Asp Pro Arg Phe Asp Ala Glu Ala Asp Gln Ile Ser Gly Phe His
    50                  55                  60

Ile Arg Ser Val Leu Cys Val Pro Ile Trp Asn Ser Asn His Gln Ile
65                  70                  75                  80

Ile Gly Val Ala Gln Val Leu Asn Arg Leu Asp Gly Lys Pro Phe Asp
                85                  90                  95

Asp Ala Asp Gln Arg Leu Phe Glu Ala Phe Val Ile Phe Cys Gly Leu
            100                 105                 110

Gly Ile Asn Asn Thr Ile Met Tyr Asp Gln Val Lys Lys Ser Trp Ala
        115                 120                 125

Lys Gln Ser Val Ala Leu Asp Val Leu Ser Tyr His Ala Thr Cys Ser
    130                 135                 140

Lys Ala Glu Val Asp Lys Phe Lys Ala Ala Asn Ile Pro Leu Val Ser
145                 150                 155                 160

Glu Leu Ala Ile Asp Asp Ile His Phe Asp Asp Phe Ser Leu Asp Val
                165                 170                 175

Asp Ala Met Ile Thr Ala Ala Leu Arg Met Phe Met Glu Leu Gly Met
            180                 185                 190

Val Gln Lys Phe Lys Ile Asp Tyr Glu Thr Leu Cys Arg Trp Leu Leu
        195                 200                 205

Thr Val Arg Lys Asn Tyr Arg Met Val Leu Tyr His Asn Trp Arg His
    210                 215                 220

Ala Phe Asn Val Cys Gln Leu Met Phe Ala Met Leu Thr Thr Ala Gly
225                 230                 235                 240

Phe Gln Asp Ile Leu Thr Glu Val Glu Ile Leu Ala Val Ile Val Gly
                245                 250                 255

Cys Leu Cys His Asp Leu Asp His Arg Gly Thr Asn Asn Ala Phe Gln
            260                 265                 270

Ala Lys Ser Gly Ser Ala Leu Ala Gln Leu Tyr Gly Thr Ser Ala Thr
        275                 280                 285

Leu Glu His His Phe Asn His Ala Val Met Ile Leu Gln Ser Glu
    290                 295                 300
```

```
Gly His Asn Ile Phe Ala Asn Leu Ser Ser Lys Glu Tyr Ser Asp Leu
305                 310                 315                 320

Met Gln Leu Leu Lys Gln Ser Ile Leu Ala Thr Asp Leu Thr Leu Tyr
                325                 330                 335

Phe Glu Arg Arg Thr Glu Phe Phe Glu Leu Val Ser Lys Gly Glu Tyr
            340                 345                 350

Asp Trp Asn Ile Lys Asn His Arg Asp Ile Phe Arg Ser Met Leu Met
        355                 360                 365

Thr Ala Cys Asp Leu Gly Ala Val Thr Lys Pro Trp Glu Ile Ser Arg
    370                 375                 380

Gln Val Ala Glu Leu Val Thr Ser Glu Phe Phe Glu Gln Gly Asp Arg
385                 390                 395                 400

Glu Arg Leu Glu Leu Lys Leu Thr Pro Ser Ala Ile Phe Asp Arg Asn
                405                 410                 415

Arg Lys Asp Glu Leu Pro Arg Leu Gln Leu Glu Trp Ile Asp Ser Ile
            420                 425                 430

Cys Met Pro Leu Tyr Gln Ala Leu Val Lys Val Asn Val Lys Leu Lys
        435                 440                 445

Pro Met Leu Asp Ser Val Ala Thr Asn Arg Ser Lys Trp Glu Glu Leu
    450                 455                 460

His Gln Lys Arg Leu Leu Ala Ser Thr Ala Ser Ser Ser Ser Pro Ala
465                 470                 475                 480

Ser Val Met Val Ala Lys Glu Asp Arg Asn
                485                 490

<210> SEQ ID NO 6
<211> LENGTH: 1784
<212> TYPE: DNA
<213> ORGANISM: Homo sapiens

<400> SEQUENCE: 6
tggaaagatg ttacttcatc tcccaggttt gctcactgca aatacaatcc tgagaactga      60
actagggcct taaagtcctg acatgcatgg cttggttttg tggattgcct ctctcaacag     120
gtggtgaaat ttaccaaatc ctttgaattg atgtccccaa agtgcagtgc tgatgctgag     180
aacagtttca agaaagcat ggagaaatca tcatactccg actggctaat aaataacagc     240
attgctgagc tggttgcttc aacaggcctt ccagtgaaca tcagtgatgc ctaccaggat     300
ccgcgctttg atgcagaggc agaccagata tctggttttc acataagatc tgttctttgt     360
gtccctattt ggaatagcaa ccaccaaata attggagtgg ctcaagtgtt aaacagactt     420
gatgggaaac ttttgatga tgcagatcaa cgacttttg aggcttttgt catcttttgt      480
ggacttggca tcaacaacac aattatgtat gatcaagtga agaagtcctg gccaagcag      540 tctgtggctc ttgatgtgct atcataccat gcaacatgtt caaaagctga agttgacaag     600
tttaaggcag ccaacatccc tctggtgtca gaacttgcca tcgatgacat tcattttgat     660
gacttttctc tcgacgttga tgccatgatc acagctgctc tccggatgtt catggagctg     720
gggatggtac agaaatttaa aattgactat gagacactgt gtaggtggct tttgacagtg     780
aggaaaaact atcggatggt tctataccac aactggagac atgccttcaa cgtgtgtcag     840
ctgatgttcg cgatgttaac cactgctggg tttcaagaca ttctgaccga ggtgaaattt     900
ttagcggtga ttgtgggatg cctgtgtcat gacctcgacc acaggggaac caacaatgcc     960
ttccaagcta agagtggctc tgccctggcc caactctatg gaacctctgc taccttggag    1020
catcaccatt tcaaccacgc cgtgatgatc cttcaaagtg agggtcacaa tatctttgct    1080
```

```
aacctgtcct ccaaggaata tagtgacctt atgcagcttt tgaagcagtc aatattggca    1140
acagacctca cgctgtactt tgagaggaga actgaattct ttgaacttgt cagtaaagga    1200
gaatacgatt ggaacatcaa aaccatcgt gatatatttc gatcaatgtt aatgacagcc     1260
tgtgaccttg gagccgtgac caaaccgtgg gagatctcca gacaggtggc agaacttgta    1320
accagtgagt tcttcgaaca aggagatcgg gagagattag agctcaaact cactccttca    1380 gcaattttg atcggaaccg gaaggatgaa ctgcctcggt tgcaactgga gtggattgat     1440
agcatctgca tgcctttgta tcaggcactg gtgaaggtca acgtgaaact gaagccgatg    1500
ctagattcag tagctacaaa cagaagtaag tgggaagagc tacaccaaaa acgactgctg    1560
gcctcaactg cctcatcctc ctcccctgcc agtgttatgg tagccaagga agacaggaac    1620
taaacctcca ggtcagctgc agctgcaaaa tgactacagc ctgaagggcc attttcagtc    1680
cagcaatgtc atccttttgt tcttttagct cagaaagacc taacatctca aggatgcact    1740
gggaaccatg cctgggcttt caccttgaag catggtcagc agca                     1784
```

<210> SEQ ID NO 7
<211> LENGTH: 194
<212> TYPE: PRT
<213> ORGANISM: Homo sapiens

<400> SEQUENCE: 7

```
Met Leu Lys Gln Ala Arg Arg Pro Leu Phe Arg Asn Val Leu Ser Ala
1               5                   10                  15

Thr Gln Trp Lys Lys Val Lys Ile Thr Arg Leu Val Gln Ile Ser Gly
            20                  25                  30

Ala Ser Leu Ala Glu Lys Gln Glu Lys His Gln Asp Phe Leu Ile Gln
        35                  40                  45

Arg Gln Thr Lys Thr Lys Asp Arg Arg Phe Asn Asp Glu Ile Asp Lys
    50                  55                  60

Leu Thr Gly Tyr Lys Thr Lys Ser Leu Leu Cys Met Pro Ile Arg Ser
65                  70                  75                  80

Ser Asp Gly Glu Ile Ile Gly Val Ala Gln Ala Ile Asn Lys Ile Pro
                85                  90                  95

Glu Gly Ala Pro Phe Thr Glu Asp Asp Glu Lys Val Met Gln Met Tyr
            100                 105                 110

Leu Pro Phe Cys Gly Ile Ala Ile Ser Asn Ala Gln Leu Phe Ala Ala
        115                 120                 125

Ser Arg Lys Glu Tyr Glu Arg Ser Arg Ala Leu Leu Glu Val Val Asn
    130                 135                 140

Asp Leu Phe Glu Glu Gln Thr Asp Leu Glu Lys Ile Val Lys Lys Ile
145                 150                 155                 160

Met His Arg Ala Gln Thr Leu Leu Lys Cys Glu Arg Cys Ser Val Leu
                165                 170                 175

Leu Leu Glu Asp Ile Glu Ser Pro Val Val Lys Phe Thr Lys Ser Phe
            180                 185                 190

Glu Leu
```

<210> SEQ ID NO 8
<211> LENGTH: 423
<212> TYPE: DNA
<213> ORGANISM: Homo sapiens

<400> SEQUENCE: 8

```
ggtccgagat gctgaagcag gcaagaagac ctttattcag aaatgtgctc agtgccacac      60
agtggaaaaa ggtgaaaatc acaagactgg tccaaatctc tggggcctct ttggctgaaa     120
aacaggaaaa gcaccaggat tttcttatac agaggcaaac aaaaacaaag gatcgacgat     180
tcaatgatga aatcgacaag ctgactggat acaagacaaa atcattattg tgcatgccta     240
tccgaagcag tgatggtgag attattggtg tgcccaagc gataaataag attcctgaag      300
gagctccatt tactgaagat gatgaaaaag ttatgcagat gtatcttcca ttttgtggaa     360
tcgccatatc taacgctcag ctctttgctg cctcaaggaa agaatatgaa agaagcagag     420
ctt                                                                   423
```

<210> SEQ ID NO 9
<211> LENGTH: 37
<212> TYPE: DNA
<213> ORGANISM: Homo sapiens

<400> SEQUENCE: 9

```
ggccacgcgt cgactagtac ttttttttt tttttt                               37
```

<210> SEQ ID NO 10
<211> LENGTH: 20
<212> TYPE: DNA
<213> ORGANISM: Homo sapiens

<400> SEQUENCE: 10

```
ggccacgcgt cgactagtac                                                 20
```

<210> SEQ ID NO 11
<211> LENGTH: 23
<212> TYPE: DNA
<213> ORGANISM: Homo sapiens

<400> SEQUENCE: 11

```
cagaacagcg ttcacatttc agc                                             23
```

<210> SEQ ID NO 12
<211> LENGTH: 24
<212> TYPE: DNA
<213> ORGANISM: Homo sapiens

<400> SEQUENCE: 12

```
aggtcagtct gttcttcaaa gagg                                            24
```

<210> SEQ ID NO 13
<211> LENGTH: 22
<212> TYPE: DNA
<213> ORGANISM: Homo sapiens

<400> SEQUENCE: 13

```
cagtaaatgg agctccttca gg                                              22
```

<210> SEQ ID NO 14
<211> LENGTH: 30
<212> TYPE: DNA
<213> ORGANISM: Homo sapiens

<400> SEQUENCE: 14

```
ttgtgcatgc ctatccgaag cagttatggt                                      30
```

<210> SEQ ID NO 15
<211> LENGTH: 25

```
<212> TYPE: DNA
<213> ORGANISM: Homo sapiens

<400> SEQUENCE: 15
gcacggtccg agatgctgaa gcagg                                            25

<210> SEQ ID NO 16
<211> LENGTH: 21
<212> TYPE: DNA
<213> ORGANISM: Homo sapiens

<400> SEQUENCE: 16
agatatctgg tctgcctctg c                                                21
```